US006824974B2

(12) United States Patent
Pisharody et al.

(10) Patent No.: US 6,824,974 B2
(45) Date of Patent: Nov. 30, 2004

(54) ELECTRONIC DETECTION OF BIOLOGICAL MOLECULES USING THIN LAYERS

(75) Inventors: Sobha M. Pisharody, Castro Valley, CA (US); Sandeep Kunwar, Redwood City, CA (US); George T. Mathai, Castro Valley, CA (US)

(73) Assignee: GenoRx, Inc., Hayward, CA (US)

( * ) Notice: Subject to any disclaimer, the term of this patent is extended or adjusted under 35 U.S.C. 154(b) by 147 days.

(21) Appl. No.: 09/970,087

(22) Filed: Oct. 2, 2001

(65) Prior Publication Data

US 2004/0146863 A1 Jul. 29, 2004

Related U.S. Application Data

(60) Provisional application No. 60/297,583, filed on Jun. 11, 2001.

(51) Int. Cl.[7] .............................. C12Q 1/00; C12Q 1/68; G01F 1/64
(52) U.S. Cl. .............................. 435/4; 435/6; 435/91.2; 536/23.1; 205/777.5
(58) Field of Search .................. 435/6, 91.2; 205/777.5; 536/23.1

(56) References Cited

U.S. PATENT DOCUMENTS

| | | |
|---|---|---|
| 5,252,294 A | 10/1993 | Kroy et al. |
| 5,466,575 A | 11/1995 | Cozzette et al. |
| 5,475,341 A | 12/1995 | Reed |
| 5,601,980 A | 2/1997 | Gordon et al. |
| 5,632,957 A | 5/1997 | Heller et al. |
| 5,653,939 A | 8/1997 | Hollis et al. |
| 5,846,708 A | 12/1998 | Hollis et al. |
| 5,945,832 A | 8/1999 | Harvey, III et al. |
| 5,965,452 A * | 10/1999 | Kovacs ..................... 436/149 |
| 6,060,023 A | 5/2000 | Maracas |
| 6,063,573 A | 5/2000 | Kayyem |
| 6,071,699 A | 6/2000 | Meade et al. |
| 6,087,100 A | 7/2000 | Meade et al. |
| 6,090,933 A | 7/2000 | Kayyem et al. |
| 6,096,273 A | 8/2000 | Kayyem et al. |
| 6,110,354 A | 8/2000 | Saban et al. |
| 6,127,127 A * | 10/2000 | Eckhardt et al. ............ 435/6 |
| 6,203,981 B1 | 3/2001 | Ackley et al. |
| 6,221,583 B1 | 4/2001 | Kayyem et al. |
| 6,221,586 B1 | 4/2001 | Barton et al. |
| 6,245,508 B1 | 6/2001 | Heller et al. |
| 6,261,776 B1 | 7/2001 | Pirrung et al. |
| 6,290,839 B1 | 9/2001 | Kayyem et al. |
| 6,303,316 B1 | 10/2001 | Kiel et al. |
| 6,320,200 B1 | 11/2001 | Reed et al. |
| 6,379,897 B1 | 4/2002 | Weidenhammer et al. |
| 6,395,480 B1 | 5/2002 | Hefti |
| 6,399,303 B1 | 6/2002 | Connolly |
| 6,429,027 B1 | 8/2002 | Chee et al. |
| 6,458,600 B1 | 10/2002 | Mirsky et al. |
| 6,461,820 B1 | 10/2002 | Barton et al. |
| 6,468,806 B1 | 10/2002 | McFarland et al. |
| 6,479,301 B1 | 11/2002 | Balch et al. |
| 2003/0064390 A1 | 4/2003 | Schülein et al. |
| 2003/0203394 A1 * | 10/2003 | Eichen et al. .................. 435/6 |

FOREIGN PATENT DOCUMENTS

| | | |
|---|---|---|
| JP | 10-146183 | 6/1998 |
| WO | WO 98/19151 | 5/1998 |
| WO | WO 99/57550 | 11/1999 |
| WO | WO 01/43870 A2 | 6/2001 |
| WO | WO 01/44501 A2 | 6/2001 |

OTHER PUBLICATIONS

Ueda et al, "Atomic force microscopy observation of deoxribonucleic acid stretched and anchored onto aluminum electrodes", Japanese J. Appl. Phys. (1999) 38(4A):2118–2119.*
Bezryadin, et la. Electrostatic trapping of single conducting nanoparticles between nonelectrodes; Appl. Phys. Lett. 71 (9); Sep. 1, 1997, p. 1273–1275.
Braun, et al.; DNA–templated assembly and electrode attachment of a conducting silver wire; Nature, vol. 391, Feb. 19, 1998; p. 775–778.
Fink, DNA and conducting electrons; CMLS, Cell. Mol. Life Sci. 58 (2001) 1–3.
Richter, Metallization of DNA; Physica E 16 (2003) 157–173.
Alexander; "Biopoly Money"; Wired Archive 8.06; Jun. 2000.
CAI et al.; "Self–Assembled DNA Networks and Their Electrical Conductivity"; Applied Physics Letters 77; Nov. 6, 2000; pp. 3105–3106.
Corby et al.; "Studies on Phosphorylation. Part X. The Preparation of Tetraesters of Pyrophosphoric Acid from Diesters of Phosphoric Acid by Means of Exchange REactions"; Journal of the Chemical Society; Apr., 1952; pp. 1234–1243.
DATTA et al.; "Current–Voltage Characteristics of Self–Assembled Monolayers by Scanning Tunneling Microscopy"; Physical Review Letters 79; Sep. 29, 1997; pp. 2530–2533.
Dill et al.; "Antigen Detection Using Microelectrode Array Microchips"; Analytica chimica Acta 444; 2001; pp. 69–78.
Eckstein et al.; "Oligonucleotide Syntheses by means of 2,2,2–Trichloroethyl Phosphorodichoridate", Angew. Chem. Internat. Edit.; vol. 6 (1967); No. 11, p. 949.
Engels; "Electrochemical Removal of Protecting Groups in Nucleotide Synthesis"; Angew. Chem. It. Ed. Engl. 18 (1979). No. 2; pp. 148–149.

(List continued on next page.)

*Primary Examiner*—Jeffrey Fredman
(74) *Attorney, Agent, or Firm*—Fenwick & West LLP

(57) ABSTRACT

This invention provides novel sensors that facilitate the detection of essentially any analyte. In general, the biosensors of this invention utilize a binding agent (e.g. biomolecule) to specifically bind to one or more target analytes. In preferred embodiments, the biomolecules spans a gap between two electrodes. Binding of the target analyte changes conductivity of the sensor thereby facilitating ready detection of the binding event and thus detection and/or quantitation of the bound analyte. A molecular sensing apparatus comprising.

76 Claims, 18 Drawing Sheets-

OTHER PUBLICATIONS

Fahlman and Sen; "DNA Conformational Switches as Sensitive Electronic Sensors and Analytes"; J. Am. Chem. Soc. 124; Apr. 2, 2002; pp. 4610–4616.

Fink and Schonenberger; "Electrical Conduction Through DNA Molecules"; Nature 398; Apr. 1, 1999; pp. 407–410.

Giese et al.; "Direct Observation of Hole Transfer Through DNA by Hopping Between Adenine Bases and by Tunneling"; Nature 412; Jul. 19, 2001; pp. 318–320.

Hianik et al.; "Amperometric Detection of DNA Hybridization on a Gold Surface Depends on the Orientation of Oligonucleotide Chains"; Biochemistry 53; 2001; pp. 199–204.

Hjort and Stafström; "Band Resonant Tunneling in DNA Molecules"; Physical Review Letters 87; Nov. 26, 2001; pp. 228101-2 through 228101-4.

Imoto et al.; "Synthesis and Antitumor Activity of N–Acetylmuramyl–$_L$–alanyl–$_D$–isoglutamine 6–Phosphate and Its Lipophilic Derivatives"; Bull. Chem. Soc. Jpn. 59 (1986); pp. 3207–3212.

Iwakuma, et al.; "Selective Removal of Protecting Groups Using Controlled Potential Electrolysis"; Journal of the American Chemical Society 94:14; Jul. 12, 1972; pp. 5139–5140.

Kasumov et al.; "Proximity–Induced Superconductivity in DNA"; Science 291; Jan. 12, 2001; pp. 280–282.

Kato et al. "Studies of Organo Sulfure Compounds. II. The Preparation and Reactions of Benzoyl Benzenethiosulfonates"; Bulletin of the Chemical Society of Japan; vol. 46 (1973), pp. 860–863.

Kelley et al.; "Single–Base Mismatch Detection Based on Charge Transduction Through DNA"; Nucleic Acids Research 27; 1999; pp. 4830–4837.

Kerr et al.; "Carbohydrates tagged with the CCo$_3$(CO)$_9$ cluster"; J. Chem. Soc., Dalton Trans.; 1999; pp. 4165–4174.

Klein et al.; "Ordered Stretching of Single Molecules of Deoxyribose Nucleic Acid Between Microfabricated Polystrene Lines"; Applied Physics Letters 78; Apr. 16, 2001; pp. 2396–2398.

Krupke et al.: "Patterning and Visualizing Self–Assembled Monolayers with Low–Energy Electrons"; Nano Letters 2; 2002; pp. 1161–1164.

Lee et al.; "Label Free Electrical Detection of DNA Hybridization by Nanogap Junction [MP 022]"; ALA, Small Talk2002, Final Program and Abstracts; Jul. 28–31, 2002.

Letsinger et al.; "Synthesis of Oligothymidylates via Phosphotriester Intermediates"; Journal of the American Chemical Society 91:12; Jun. 4, 1969; pp. 3350–3355.

Lewis et al.; "Distance–Dependent Electron Transfer in DNA Hairpins"; Science 277; Aug. 1, 1997; pp. 673–676.

Maia et al.; "Mild Reductive Cleavage of Tryptophane and Histidine Side–Chain Protecting Groups"; Eur. J. Org. Chem 2001; pp. 1967–1970.

Mahieu, et al.; "Synthesis of New Thiosulfonates and Disulfides from Sulfonyl Chlorides and Thiols"; Synthetic Communications 16(13); (1986); pp. 1709–1722.

Mairanovsky; "Electro–Deprotection—Electrochemical Removal of Protecting Groups"; Angew. Chem. Int. Ed. Engl. 15; (1976); pp. 281–292.

Nyasse, et al.; "Synthesis and cathodic cleavage of a set of substituted benzenesulfonamides including the corresPonding tert–butyl sulfonylcarbamates; p$\kappa_a$ of sulfonamides"; J. Chem. Soc. Perkin Trans. I; 1995; pp. 2025–2031.

Okahata et al.; "Anisotropic Electric Conductivity in an Aligned DNA Cast Film"; J. Am. Chem Soc. 120; Jun. 5, 1998; pp. 6165–6166.

Park et al.; "Array–Based Electrical Detection of DNA with Nanoparticle Probes"; Science 295; Feb. 22, 2002; pp. 1503–1506.

Porath et al.; "Direct Measurement of Electrical Transport through DNA Molecules"; Nature 403; Feb, 10, 2000; pp. 635–638.

Püschl et al.; "Solution Phase Synthesis of Dithymidine Phosphorothioate by a Phosphotriester Method Using New S–Protecting Groups"; Nucleosides & Nucleotides 16; 1997; pp. 145–158.

Trans et al.; "Potential Modulations Along Carbon Nanotubes"; Nature 404; Apr. 2000; pp. 834–835.

Trigalo et al.; "Chemistry of Bacterial Endotoxins. Part 4. Synthesis f Anomeric 2–Deoxy–2–[(3R)–3–hydroxytetradecanimido]–D–gluc pyranosyl Phosphate and Pyrophosphate Derivatives Related to 'Lipid A'"; J. Chem. Soc. Perkin Trans. I; 1988; pp. 2243–2249.

Umek et al.; "Electronic Detection of Nucleic Acids a Versatile Platform for Molecular Diagnostics"; Journal of Molecular Diagnostics 3; May 2001; pp. 74–84.

Warman et al.; "DNA: A Molecular Wire?"; Chemical Physics Letters 249; Feb. 9, 1996; pp. 319–322.

Watson et al.; "Technology for Microarray Analysis of Gene Expression"; Current Opinion in Biotechnology 9: 1998; pp. 609–614.

Whitesides et al.; "Wet Chemical Approaches to the Characterization of Organic Surfaces: Self–Assembled Monolayers, Wetting, and the Physical–Organic Chemistry of the Solid–Liquid Interface"; Langmuir 6; 1990; pp. 87–96.

Yu et al; "Electronic Detection of Single–Base Mismatches in DNA with Ferrocene–Modified Probes"; J. Am. Chem. Soc. 123; 2001; pp. 11155–11161.

* cited by examiner

Conductor 1 position deposition mask

Conductor 2 position deposition

Conductor 2 position deposition mask

ELECTRONIC DETECTION OF BIOLOGICAL MOLECULES USING THIN LAYERS

CROSS-REFERENCE TO RELATED APPLICATIONS

This application claims priority to and benefit of U.S. S No. 60/297,583, filed on Jun. 11, 2001, which is incorporated herein by reference in its entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention pertains to a biosensor for detecting and/or quantifying analytes. More particularly, this invention pertains to a biosensor based on a detection element that is a single macromolecule spanning two electrodes.

BACKGROUND OF THE INVENTION

Biosensors are devices that can detect and/or quantify analytes using known interactions between a targeted analyte and a binding agent that is typically a biological macromolecule such as an enzyme, receptor, nucleic acid, protein, lectin, or antibody. Biosensors have applications in virtually all areas of human endeavor. For example, biosensors have utility in fields as diverse as blood glucose monitoring for diabetics, the recognition of poisonous gas and/or explosives, the detection of chemicals commonly associated with spoiled or contaminated food, genetic screening, environmental testing, and the like.

Biosensors are commonly categorized according to two features, namely, the type of macromolecule utilized in the device and the means for detecting the contact between the binding agent and the targeted analyte. Major classes of biosensors include enzyme (or catalytic) biosensors, immunosensors and DNA biosensors.

Enzyme (or catalytic) biosensors typically utilize one or more enzymes as the macromolecule and take advantage of the complimentary shape of the selected enzyme and the targeted analyte. Enzymes are proteins that perform most of the catalytic work in biological systems and are known for highly specific catalysis. The shape and reactivity of a given enzyme limits its catalytic activity to a very small number of possible substrates. Enzyme biosensors rely on the specific chemical changes related to the enzyme/analyte interaction as the means for recognizing contact with the targeted analyte. For example, upon interaction with an analyte, an enzyme biosensor may generate electrons, a colored chromophore or a change in pH as the result of the relevant enzymatic reaction. Alternatively, upon interaction, with an analyte, an enzyme biosensor may cause a change in a fluorescent or chemiluminesceint signal that can be recorded by an appropriate detection system.

Immunosensors utilize antibodies as binding agents. Antibodies are protein molecules that generally do not perform catalytic reactions, but specifically bind to particular "target" molecules (antigens). Antibodies are quite specific in their interactions and, unlike most enzymes, they are capable of recognizing and selectively binding to very large bodies such as single cells. Thus, in addition to detection of small analytes, antibody-based biosensors allow for the identification of certain pathogens such as dangerous bacterial strains.

DNA biosensors typically utilize the complimentary nature of the DNA or RNA double-strands and are designed for the specific detection of particular nucleic acids. A DNA biosensor sensor generally uses a single-stranded DNA as the binding agent. The nucleic acid material in a given test sample is placed into contact with the binding agent under conditions where the biosensor DNA and the target nucleic acid analyte can form a hybrid duplex. If a nucleic acid in the test sample is complementary to a nucleic acid used in the biosensor, the two interact/bind. The interaction can be monitored by various means such as a change in mass at the sensor surface or the presence of a fluorescent or radioactive signal. In alternative arrangements, the target nucleic acid(s) are bound to the sensor and contacted with labeled probes to allow for identification of the sequence(s) of interest.

While the potential utility for biosensors is great and while hundreds of biosensors have been described in patents and in the literature, actual commercial use of biosensors remains limited. Aspects of biosensors that have limited their commercial acceptance include a lack the sensitivity and/or speed of detection necessary to accomplish certain tasks, problems with long term stability, difficulty miniaturizing the sensor, and the like. In addition, a number of biosensors must be pre-treated with salts and/or enzyme cofactors, a practice that is inefficient and bothersome.

SUMMARY OF THE INVENTION

This invention pertains to the development of a novel molecular sensing apparatus (biosensor) and to methods of use thereof. In preferred embodiments, the sensing apparatus comprises a first electrode, a second electrode, an insulator between the first electrode and the second electrode; and a binding agent (e.g. a biological macromolecule) connecting the first electrode and the second electrode. In particularly preferred embodiments, the binding agent is attached to the electrode in a manner that permits charge to flow from the electrode to the binding agent or from the binding agent to the electrode. Preferred binding agents include, but are not limited to, biological macromolecules (e.g. a nucleic acid, a protein, a polysaccharide, a lectin, a lipid, etc.) with a nucleic acid being most preferred. While the nucleic acid can be essentially any length, preferred nucleic acids range in length from about 5 nucleotides to about 5,000 nucleotides, more preferably from about 8 nucleotides to about 1,000 nucleotides or 500 nucleotides, still more preferably from about 10 nucleotides to about 300 nucleotides, and most preferably from about 15, 20, 25, 30 or 50 nucleotides to about 100 nucleotides or 150 nucleotides in length. Typically, the nucleic acid is of sufficient length to specifically hybridize to a target nucleic acid in a complex population of nucleic acids (e.g. total genomic DNA) under stringent conditions.

In preferred embodiments, the biological macromolecule is functionalized with a chemical group thereby facilitating the attachment of the macromolecule to the electrode(s). Preferred chemical groups include, but are not limited to a sulfate, a sulfhydryl, an amine, an aldehyde, a carboxylic acid, a phosphate, a phosphonate, an alkene, an alkyne, a hydroxyl group, a bromine, an iodine, a chlorine, a light-activatable (labile) group, a group activatable by an electric potential, and the like. In certain embodiments, the biological macromolecule is functionalized with a second biological macromolecule (e.g. a receptor, a receptor ligand, an antibody, an epitope, a nucleic acid, a lectin, a sugar, and the like). In preferred embodiments, however, such second biological macromolecules exclude nucleic acids.

Preferred insulators are insulators having a resistivity greater than about $10^{-3}$ ohm-meters, more preferably greater than about $10^{-2}$ ohm-meters, and most preferably greater than about $10^{-1}$, 1, or 10 ohm-meters. Suitable insulators include, but are not limited to $SiO_2$, $TiO_2$, $ZrO_2$, quartz, porcelain, ceramic, polystyrene, Teflon (other high-resistivity plastics), an insulating oxide or sulfide of a transition metal in the periodic table of the elements, and the like.

In certain preferred embodiments, the first electrode and the second electrode are separated by a distance in the range of 1 to $10^{10}$ Angstroms. Typically the first electrode and the second electrode are separated by a distance less than about 300 Angstroms, preferably less than about 150 Angstroms, more preferably less than about 70 Angstroms, and most preferably less than about 50 angstroms.

In certain embodiments, the first electrode and/or the second electrode have a resistivity of less than about $10^{-2}$ ohm-meters, preferably less than about $10^{-3}$ ohm-meters, more preferably less than about $10^{-4}$ ohm-meters, and most preferably less than about $10^{-5}$, or $10^{-6}$ ohm-meters. Particularly preferred electrodes comprise a material such as ruthenium, osmium, cobalt, rhodium, rubidium, lithium, sodium, potassium, vanadium, cesium, beryllium, magnesium, calcium, chromium, molybdenum, silicon, germanium, aluminum, iridium, nickel, palladium, platinum, iron, copper, titanium, tungsten, silver, gold, zinc, cadmium, indium tin oxide, carbon, or a carbon nanotube. In certain preferred embodiments, the first electrode is functionalized to contain a chemical group that can be derivatized or crosslinked (e.g., a sulfate, a sulfhydryl, an amine, an aldehyde, a carboxylic acid, a phosphate, a phosphonate, an alkene, an alkyne, a hydroxyl group, a bromine, an iodine, a chlorine, a light-activatable group, a group activatable by an electric potential, etc.). The first and/or second electrode can bear a self-assembled monolayer (SAM). Particularly preferred SAMs comprise a compound selected from the group consisting of an alkanethiol, a phospholipid, a bola amphiphile, and an oligo(phenylenevinylene).

In a particularly preferred embodiment, the biological macromolecule is attached to the first and/or to the second electrode directly by a thiol group or through a linker bearing a thiol group. In another particularly preferred embodiment, the biological macromolecule is attached to the first and/or to the second electrode directly by a phosphonate or through a linker bearing a phosphonate. In preferred embodiments, the biological macromolecule is attached to the first and/or to the second electrode by a linker (e.g., DFDNB, DST, ABH, ANB-NOS, EDC, NHS-ASA, SIA, oligo(phenylenevinylene), etc.).

The apparatus can further comprise a substrate (other than the electrode and/or insulator) where the first electrode and the second electrode are integrated with the substrate. In certain embodiments, the first electrode and the second electrode are integrated with the insulator to form a substrate. The electrodes can be formed in essentially any desired shape (e.g. convex, concave, textured, corrugated, patterned uniformly, randomly patterned, etc.). Certain preferred electrode orientations include annular, planar, and orthogonal. In certain embodiments, the first electrode comprises a first surface and a second electrode comprises a second surface where the first surface and the second surface are not co-planar.

The apparatus can comprise a plurality of electrode pairs. Thus, in certain embodiments, the first electrode and the second electrode comprise a first electrode pair, and the molecular sensing apparatus further comprises a second electrode pair comprising a second first electrode and a second second electrode. In certain embodiments, the apparatus comprises at least 3, preferably at least 10 or 20, more preferably at least 50, 100, or 1,000, and most preferably at least 10,000 or at least 1,000,000 electrode pairs.

In certain embodiments, the apparatus further comprises a measurement device electrically coupled to the first electrode and to the second electrode of at least one said electrode pair. Preferred measurement devices measure an electromagnetic property selected from the group consisting direct electric current, alternating electric current, permitivity, resistivity, electron transfer, electron tunneling, electron hopping, electron transport, electron conductance, voltage, electrical impedance, signal loss, dissipation factor, resistance, capacitance, inductance, magnetic field, electrical potential, charge and magnetic potential. One particularly preferred measurement device is a potentiostat.

The apparatus can further comprise an electrical circuit electrically coupled to the first electrode and the second electrode. One such circuit comprises an electrical signal gating system (e.g. a CMOS gating system), and/or a voltage source, and/or a multiplexor, and/or a computer.

In certain embodiments, the electrodes comprising the first and second electrode pairs have attached the same (species of) biological macromolecule. In certain embodiments, different electrode pairs, have attached different biological molecules.

In certain embodiments, the first electrode and/or the second electrode comprise a semi-conducting material. Preferred semiconducting materials have a resistivity ranging from about $10^{-6}$ ohm-meters to about $10^{-7}$ ohm-meters. Preferred semiconducting materials include, but are not limited to silicon, dense silicon carbide, boron carbide, $Fe_3O_4$, germanium, silicon germanium, silicon carbide, tungsten carbide, titanium carbide, indium phosphide, gallium nitride, gallium phosphide, aluminum phosphide, aluminum arsenide, mercury cadmium telluride, tellurium, selenium, ZnS, ZnO, ZnSe, CdS, ZnTe, GaSe, CdSe, CdTe, GaAs, InP, GaSb, InAs, Te, PbS, InSb, PbTe, PbSe, and tungsten disulfide.

In one embodiment, the apparatus comprises: a first electrode having a first surface; a second electrode having a second surface coplanar to the first surface; an insulator between said first surface and said second surface; and a nucleic acid joining the first electrode to said second electrode.

This invention also provides a method of making a molecular sensing apparatus. In certain embodiments, the method comprises: providing a first electrode and a second electrode separated by an insulator; contacting the first and the second electrode with a first solution comprising a biological macromolecule (e.g., a nucleic acid); placing a charge on the first electrode to attract the biological macromolecule to the first electrode where the macromolecule attaches to the first electrode to form an attached macromolecule; and placing a charge on the second electrode to attract a portion of the attached macromolecule to the second electrode to attach the macromolecule to the second electrode. Preferred macromolecules, electrodes, electrode configurations, insulators, measurement devices, circuits, and the like, include, but are not limited to those described above. Where the apparatus comprises multiple electrode pairs, the method can further comprise contacting a second electrode pair with a second solution comprising a second biological macromolecule; placing a charge on the first electrode of the second electrode pair to attract the second biological macromolecule to the first electrode of the second electrode pair whereby the second biological macromolecule attaches to said first electrode to form an attached second macromolecule; and placing a charge on the second electrode of said second electrode pair to attract a portion of said attached second macromolecule to attach said second macromolecule to said second electrode of said second electrode pair. The first and second solution can be the same or different. Similarly, the first biological macromolecule and the second biological macromolecule can be the same or different.

In still another embodiment, this invention provides a method of detecting an analyte. The method involves i) providing a molecular sensing apparatus comprising a first electrode and a second electrode separated by an insulator where said first electrode has a biological macromolecule attached thereto; ii) contacting the attached macromolecule with said analyte whereby said analyte binds to said macromolecule thereby forming a macromolecule/analyte complex; iii) placing a charge on said second electrode to attract a portion of said bound analyte to said second electrode where said second analyte is bound to the second electrode such that the macromolecule/analyte complex forms a connection between the first electrode and the second electrode; and iv) detecting the connection between said first and said second electrode. In certain embodiments, the providing comprises: contacting the first electrode with a first solution comprising the biological macromolecule; and placing a charge on the first electrode whereby the charge attracts the biological macromolecule to the electrode and the biological macromolecule attaches to the electrode. Where multiple electrode pairs are present, the method can involve repeating these steps for each electrode pair. The "placing a charge" can, optionally involve placing a charge on the first electrode opposite to the charge on the second electrode. In certain embodiments, the "detecting" comprises detecting an electromagnetic property selected from the group consisting of direct electric current, alternating electric current, permittivity, resistivity, electron transfer, electron tunneling, electron hopping, electron transport, electron conductance, voltage, electrical impedance, signal loss, dissipation factor, resistance, capacitance, inductance, magnetic field, electrical potential, charge, and magnetic potential. Preferred macromolecules, electrodes, electrode configurations, insulators, measurement devices, circuits, and the like, include, but are not limited to those described above.

In still another embodiment, this invention provides a method of detecting an analyte, where the method involves: i) providing a molecular sensing apparatus comprising a first electrode and a second electrode separated by an insulator where the first electrode has a first biological macromolecule attached thereto and the second electrode has a second biological macromolecule attached thereto; ii) contacting the first attached macromolecule and the second attached macromolecule with the analyte whereby said analyte binds to the first macromolecule and to the second macromolecule thereby forming a macromolecule/analyte complex forming a connection between said first electrode and said second electrode; and iii) detecting the connection between said first and said second electrode. In certain embodiments, the "providing" comprises contacting the first electrode with a first solution comprising the first biological macromolecule; and placing a charge on the first electrode whereby the charge attracts the first biological macromolecule to the electrode and the biological macromolecule attaches to the electrode. Similarly, in certain embodiments, the "providing" comprises contacting the second electrode with a solution comprising the second biological macromolecule; and placing a charge on the second electrode whereby the charge attracts the second biological macromolecule to the second electrode and the second biological macromolecule attaches to the second electrode. In certain embodiments, the "detecting" comprises detecting an electromagnetic property selected from the group consisting of direct electric current, alternating electric current, permitivity, resistivity, electron transfer, electron tunneling, electron hopping, electron transport, electron conductance, voltage, electrical impedance, signal loss, dissipation factor, resistance, capacitance, inductance, magnetic field, electrical potential, charge, and magnetic potential. Preferred macromolecules, electrodes, electrode configurations, insulators, measurement devices, circuits, and the like, include, but are not limited to those described above.

This invention provides still another method of detecting an analyte. The method involves i) providing a molecular sensing apparatus comprising a first electrode and a second electrode separated by an insulator where a biological macromolecule forms a connection between the first electrode and the second electrode; ii) detecting the connection between the first and the second electrode; iii) contacting the biological macromolecule (binding agent) with the analyte whereby the analyte binds to the macromolecule thereby forming a macromolecule/analyte complex; and iv) detecting a difference in the connection between the first electrode and the second electrode. In certain embodiments, the "contacting" comprises placing a charge on the first and/or the second electrode whereby the charge attracts the analyte to the biological macromolecule. In certain embodiments, the "providing" comprises contacting the first electrode with a first solution comprising the biological macromolecule; and placing a charge on the first electrode whereby the charge attracts the biological macromolecule to the electrode and the biological macromolecule attaches to the electrode; and placing a charge on the second electrode to attract a portion of the bound macromolecule to the second electrode where the macromolecule is bound to the second electrode such that the macromolecule forms a connection between the first electrode and said second electrode. In certain embodiments, the "placing a charge" comprises placing a charge on the first electrode opposite to the charge on the second electrode. The "detecting" can comprise detecting an electromagnetic property selected from the group consisting of direct electric current, alternating electric current, permitivity, resistivity, electron transfer, electron tunneling, electron hopping, electron transport, electron conductance, voltage, electrical impedance, signal loss, dissipation factor, resistance, capacitance, inductance, magnetic field, electrical potential, charge and magnetic potential. In particularly preferred embodiments, the biological macromolecule is attached to the first electrode by an electrically conductive linker. In certain embodiments, the binding agent is a nucleic acid and the analyte is a protein or a protein complex. Preferred macromolecules, electrodes, electrode configurations, insulators, measurement devices, circuits, and the like, include, but are not limited to those described above.

Any of the methods and devices described herein include embodiments where the binding agents are not joined to the first electrode and/or the second electrodes a second or third nucleic acid. Thus, in such embodiments, where the binding agent is a nucleic acid, a single nucleic acid molecule spans the first and second electrode and linkers or functional groups, if present, are not themselves nucleic acids.

Definitions

The term "biosensor" refers to a sensor that uses a biological macromolecule (e.g. nucleic acid, carbohydrate, protein, antibody, etc.) to specifically recognize/bind to a target analyte. The term "molecular sensing apparatus" is used interchangeably with the term "biosensor".

The term "biological macromolecule" as used herein refers to a biological molecule such as a nucleic acid, protein, antibody, carbohydrate, polysaccharide, lipid, and the like.

The term "electrically conductive" wherein used with reference to a linker, molecule or molecular complex refers to the ability of that linker, molecule or molecular complex to pass charge through itself. Preferred electrically conductive molecules have a resistivity lower than about $10^{-3}$ more preferably lower than about $10^{-4}$, and most preferably lower than about $10^{-6}$ or $10^{-7}$ ohm-meters.

The term "electrically coupled" binding agent and an electrode refers to an association between that binding agent and the electrode such that electrons can move from the binding agent to the electrode or from the electrode to the binding agent. Electrical coupling can include direct covalent linkage between the binding agent and the electrode, indirect covalent coupling (e.g. via a linker), direct or indirect ionic bonding between the binding agent and the electrode, or other bonding (e.g. hydrophobic bonding). In addition, no actual bonding may be required and the binding agent can simply be contacted with the electrode surface.

The term "sensor element" as used herein refers to a pair of electrodes (e.g. first electrode 10 and second electrode 12) and associated binding agent(s) 14 that, when bound by an analyte form a molecular complex that spans the pair of electrodes.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189–197. Other synthetic backbones encompasses by the term include methyl-phosphonate linkages or alternating methylphosphonate and phosphodiester linkages (Strauss-Soukup (1997) Biochemistry 36: 8692–8698), and benzylphosphonate linkages (Samstag (1996) Antisense Nucleic Acid Drug Dev 6: 153–156). The term nucleic acid is used interchangeably with gene, cDNA, mRNA, oligonucleotide primer, probe and amplification product.

The term "antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An exemplary immunoglobulin (antibody) structural unit comprises a tetramer. Each tetramer is composed of two identical pairs of polypeptide chains, each pair having one "light" (about 25kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab. with part of the hinge region (see, Fundamental Immunology, Third Edition, W. E. Paul, ed., Raven Press, N.Y. 1993). While various antibody fragments are defined in terms of the digestion of an intact antibody, one of skill will appreciate that such fragments maybe synthesized de novo either chemically or by utilizing recombinant DNA methodology. Thus, the term antibody, as used herein, also includes antibody fragments either produced by the modification of whole antibodies, those synthesized de novo using recombinant DNA methodologies (e.g., single chain Fv), and those found in display libraries (e.g. phage display libraries).

The phrases "hybridizing specifically to" or "specific hybridization" or "selectively hybridize to", refer to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target sequence, and to a lesser extent to, or not at all to, other sequences. "Stringent hybridization" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 Overview of principles of hybridization and the strategy of nucleic acid probe assays, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning—A Laboratory Manual* (2nd ed.) Vol. 1–3, Cold Spring Harbor Laboratory, Cold Spring Harbor Press, N.Y., (Sambrook et al.) supra for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

In one particularly preferred embodiment, stringent conditions are characterized by hybridization in 1 M NaCl, 10 mM Tris-HCl, pH 8.0, 0.01% Triton X-100, 0.1 mg/ml fragmented herring sperm DNA with hybridization at 45° C. with rotation at 50 RPM followed by washing first in 0.9 M NaCl, 0.06 M NaH2PO4, 0.006 M EDTA, 0.01% Tween-20 at 45° C. for 1 hr, followed by 0.075 M NaCl, 0.005 M NaH2PO4, 0.5 mM EDTA at 45° C. for 15 minutes.

A "high resistivity plastic" refers to a plastic with a resistivity greater than about $10^{-3}$ ohm-meters, more preferably greater than about $10^{-2}$ ohm-meters, and most preferably greater than about $10^{-1}$, 1 or 10 ohm-meters.

BRIEF DESCRIPTION OF THE DRAWINGS

FIG. 4A shows a top view, while FIG. 4B illustrates a side view.

DETAILED DESCRIPTION

This invention pertains to a novel sensors (biosensors) that are useful for detecting a wide range of analytes. The sensors utilize a binding agent (e.g. a biomolecule) to specifically bind to one or more target analytes and thereby confer specificity and selectivity. In preferred embodiments, the binding agent (e.g. biomolecule) spans a gap between two electrodes. Binding of the target analyte changes conductivity, or other electrical properties, of the sensor thereby facilitating ready detection of the binding event and thus detection and/or quantitation of the bound analyte. Because the biosensors of this invention provide a change in conductance or charge flow when bound by the target analyte, they are easily read using electronic/electrochemical means and do not require the use of detectable labels.

I. Sensor Element Configuration

Figure 1:
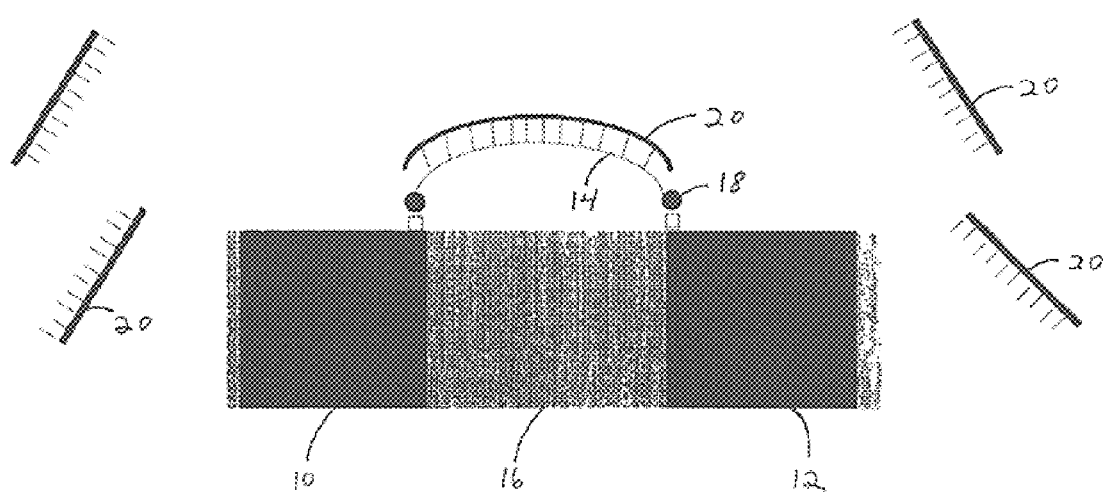
FIG. 1 illustrates a basic biosensor of this invention. The sensor element comprises two electrodes 10 and 12 connected by a binding agent (e.g. a biomolecule). Binding of the analyte to the binding agent forms a binding agent/analyte complex spanning the electrodes. The complex is easily detected using, e.g. electrical means.

One embodiment of a basic biosensor (molecular sensing apparatus) of this invention is schematically illustrated in FIG. 1. The sensor comprises a first electrode 10, a second electrode 12, and a binding agent (e.g. biomolecule) 14 spanning the gap between the two electrodes. The two electrodes can be separated by an air gap, however, in preferred embodiments, the electrodes are separated by a spacer 16 (e.g. an insulator, a dielectric, or a semiconductor). The binding agent 14 can be directly bound to the electrodes or it can be coupled to the first electrode 10 and/or the second electrode 12 through one or more linkers or functional groups 18. The binding agent 14 is attached to the electrodes in a manner that leaves sufficient area of the sensor molecule free to bind with its "cognate" target molecule 20 (the target analyte).

In one embodiment, the binding agent 14 is a single-stranded nucleic acid. The nucleic acid is derivatized at each terminus with a linker that physically and electrically couples the nucleic acid to the respective electrodes 10 and 12 such that the nucleic acid spans the gap between the electrodes. Single-stranded nucleic acids are essentially non-conductive. However, when the nucleic acid binding agent is contacted with a complementary nucleic acid analyte under conditions that permit nucleic acid hybridization, the analyte nucleic acid binds to the sensor nucleic acid via complementary base pairing to form a double stranded hybrid, duplex spanning the electrodes. This double stranded duplex is electrically conductive. The change in conductivity caused by such binding is readily detected using electrical/electrochemical means.

The binding agent is not limited to a nucleic acid. Any number of other binding agents can also be used in such a biosensor. Generally, binding agents are selected that are capable of specifically binding to a particular target analyte. Such binding agents include, but are not limited to proteins, antibodies, lectins, sugars, polysaccharides, and the like.

While, in preferred embodiments, binding agents are utilized that are non-conductive by themselves, but form an electrically conductive complex when bound to the target analyte. The sensors of this invention are not limited to such molecules. In certain embodiments it is sufficient that the analyte/binding agent complex simply show a different conductivity than the binding agent alone.

Alternatively, where the analyte/binding agent complex shows the same conductivity as the binding agent alone, it is possible to use various chemical agents that intercalate into the analyte/binding agent complex and change the effective conductivity of that complex. There are typically intercalation sites, or fewer sites afforded by the binding agent alone. Thus, the analyte binding complex, by intercalating a greater number of such agents shows a different conductivity.

Intercalating reagents that change the conductivity of a biomolecule or molecular complex are well known to those of skill in the art. Such intercalators include, but are not limited to redox-active cations (e.g. $Ru(NH_3)_6^{3+}$) and various transition metal/ligand complexes. Transition metals are those whose atoms have an incomplete shell of electrons. Suitable transition metals for use in the invention include, but are not limited to, cadmium (Cd), magnesium (Mg), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), vanadium (V), chromium (Cr), manganese (Mn), nickel (Ni), molybdenum (Mo), technetium (Tc), tungsten (W), and iridium (Ir). That is, the first series of transition metal, the platinum metals (Ru, Rh, Pd, Os, Ir and Pt), along with Re, W, Mo and Tc, are preferred. Particularly preferred are ruthenium, rhenium, osmium, platinum and iron.

The transition metals are complexed with a variety of ligands to form suitable transition metal complexes, as is well known in the art. Suitable ligands include, but are not limited to, —$NH_2$; pyridine; pyrazine; isonicotinamide; imidazole; bipyridine and substituted derivative of bipyridine; phenanthrolines, particularly 1,10-phenanthroline (abbreviated phen) and substituted derivatives of phenanthrolines such as 4,7-dimethylphenanthroline; dipyridophenazine; 1,4,5,8,9,12-hexaazatriphenylene (abbreviated hat); 9,10-phenanthrenequinone diimine; 1,4,5,8-tetraazaphenanthrene (abbreviated tap); 1,4,8,11-tetraazacyclotetradecane; diaminopyridine (abbreviated damp); porphyrins and substituted derivatives of the porphyrin family.

Such intercalating reagents can also be used to detect mismatches between the binding agent and the target analyte. Thus, for example where the binding agent and the analyte are nucleic acids, intercalating reagents comprising dimeric naphthyridines will specifically intercalate and localize where there is a G-G mismatch between the binding reagent and the target analyte (see, e.g., Nakatani et al. (2001) *Nature/Biotechnology*, 19(1): 51–55). Such mismatch specific reagents can be used to detect or screen for single nucleotide polymorphisms (SNPs).

While FIG. 1 illustrates essentially a single sensor element of this invention, various embodiments contemplate the use of a multiplicity of sensor elements. Thus, in various embodiments, there can exist multiple binding agents 14 spanning a single pair of electrodes and/or a multiplicity of electrode pairs 20 each electrode pair being spanned by one or more binding agents 14. Because of the small size of the sensor element, a large number of sensor elements can be placed in a relatively small area (e.g. on a chip) thereby increasing sensitivity and improving signal to noise (S/N) ratio. In addition, assays can be performed using small quantities of sample. A single substrate/chip can incorporate a number of different sensor elements facilitating detection/quantification of a number of different analytes.

Figure 2A:
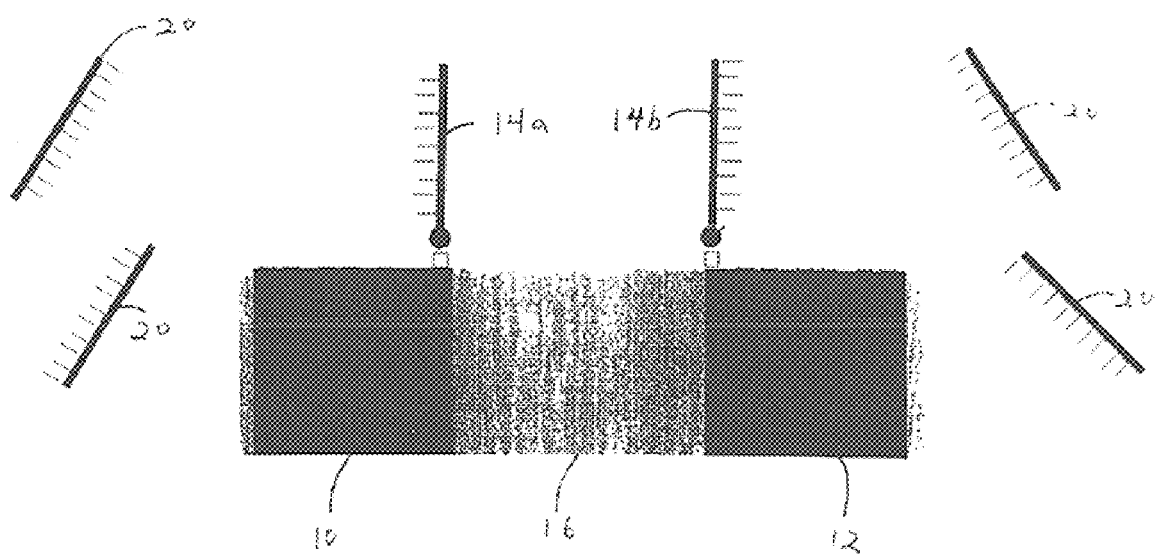
FIGS. 2A and 2B illustrate an embodiment of the biosensor comprising two binding agents, 14a and 14b, one on each electrode (FIG. 2B). The two binding agents are bound by the analyte forming a binding agent/analyte complex spanning the electrodes. The complex is easily detected using, e.g. electrical means.
Figure 2B:
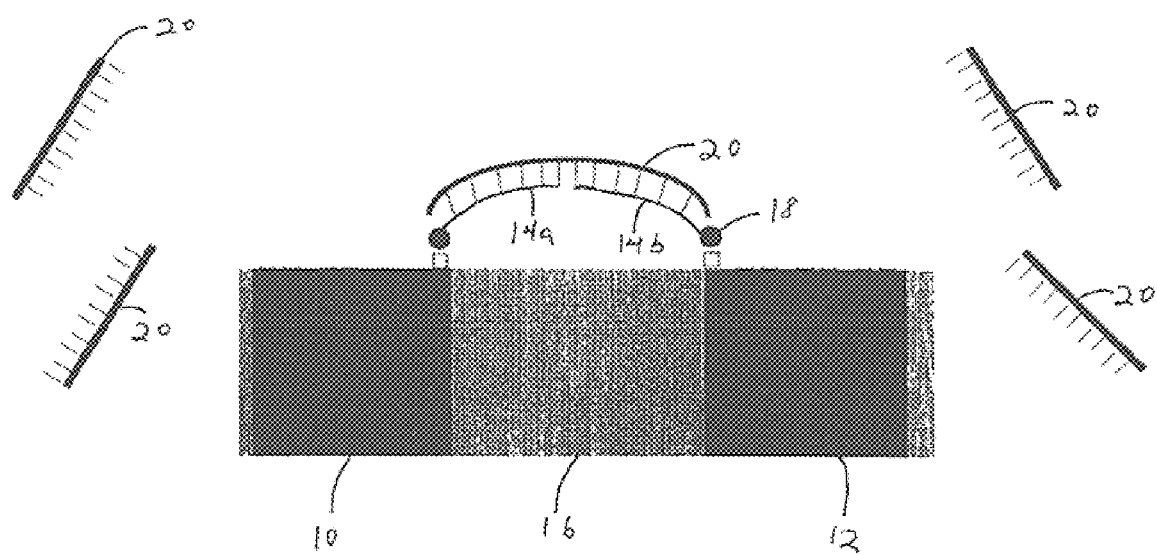

The sensor elements can adopt a wide variety of configurations. Thus, for example, in another embodiment illustrated in FIGS. 2A and 2B, the electrodes are not spanned by a single binding agent. Rather, a first binding agent 14a is attached to the first electrode 10 and a second binding agent 14b is attached to the second electrode 12 (FIG. 2A). Binding of the analyte 20 to the two binding agents creates an electrically conductive moiety that spans the gap between the two electrodes allowing current to flow between the electrodes and thereby facilitating detection/quantification of the bound analyte.

Thus, for example, in one embodiment, the first and second binding agents are each nucleic acids complementary to half of the target analyte. When the analyte contacts the binding agents under conditions permitting hybridization, the two binding agents hybridize to the analyte forming a double-stranded nucleic acid spanning the two electrodes (see, e.g., FIG. 2B).

Figure 3A:
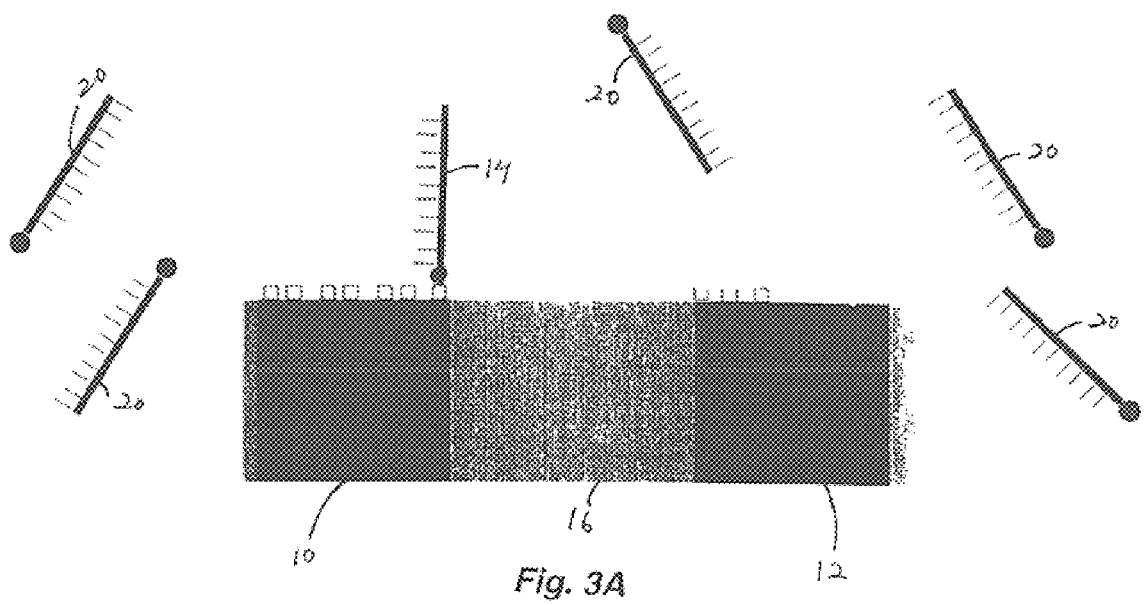
FIGS. 3A and 3B illustrate an embodiment of the biosensor comprising a binding agent attached to a first electrode 10 of a pair of electrodes (FIG. 3A). The analyte binds to the binding agent and to the second electrode 12 analyte forming a binding agent/analyte complex spanning the electrodes. The complex is easily detected using, e.g. electrical means.
Figure 3B:
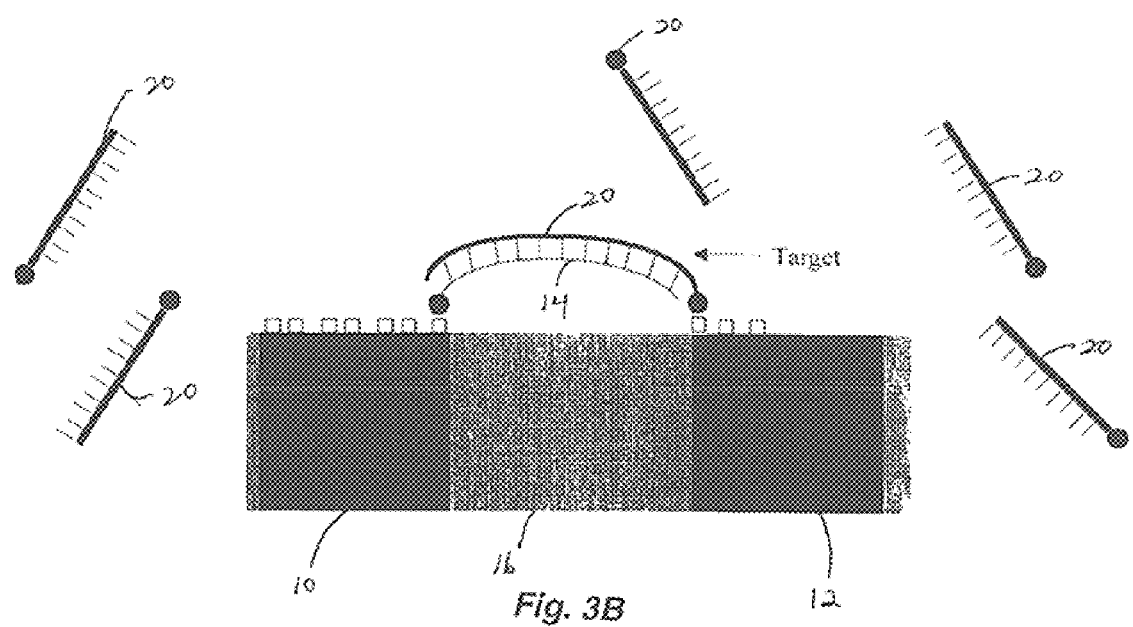

Still another preferred embodiment is illustrated in FIGS. 3A and 3B. In this embodiment, a binding agent 14 is attached to a first electrode 10 (FIG. 3A). The target analyte is tagged with a moiety that causes the analyte to interact with and/or bind to a second electrode. In use, the analyte 20 binds to, e.g. the second electrode 12 and is bound by the biological molecule 14. Together the binding agent 14 and the analyte 20 bridge the gap between the electrodes resulting in a detectable change in conductance.

In certain embodiments, the analyte is allowed to contact the binding agent and form a binding agent/analyte complex. Then application of a charge to the second electrode (and, optionally, an opposite charge to the first electrode) draws the analyte or a portion thereof to the second electrode whereby the analyte, or a linker or functional group of the analyte and/or the electrode causes the analyte to be linked to the second electrode thereby forming the analyte/binding agent complex spanning the two electrodes.

These configurations are simply illustrative of certain preferred embodiments of this invention. Using the teaching provided herein, other sensor element configurations can be readily developed by one of ordinary skill in the art.

While each electrode (electrode pair) can bear a single binding agent 14, typically, each electrode (electrode pair) bears a plurality of binding agents 14. Thus, in preferred embodiments, each electrode or electrode pair bears at least two, preferably at least 10, more preferably at least 50, still more preferably at least 100, and most preferably at least 1,000, at least 10,0000, at least 100,0000, or at least 1,000,000 binding agents (e.g., biomolecules) 14.

The electrodes comprising an electrode pair (sensor element) can be of any convenient dimension. In preferred embodiments, the electrodes comprising an electrode pair are spaced such that the analyte and/or the analyte/binding agent combination span the gap between the electrodes. In certain embodiments, the electrodes are separated by a distance ranging from about 1 Angstrom to about $10^{10}$ Angstroms, preferably from about 10 Angstroms to about $10^5$ Angstroms, more preferably from about 25 Angstroms to about $10^4$ Angstroms, and most preferably from about 40 Angstroms to about Angstroms. Preferred interelectrode spacings are less than about 200 Angstroms, preferably less than about 150 Angstroms, more preferably less than about 100 Angstroms, and most preferably less than about 50 Angstroms, about 40 Angstroms or about 30 Angstroms.

The gap between the electrodes can be an air gap, filled with oxygen or with an inert gas (e.g. argon, etc.), a vacuum, or the gap can be filled with an insulator, semiconductor, or a dielectric. In preferred embodiments, the gap between the electrodes is filled with an insulator. Preferred insulators include elements, compounds or substances that have a resistivity greater than about $10^{-3}$ ohm-meters, preferably greater than about $10^{-2}$ ohm-meters, more preferably greater than about $10^{-1}$ ohm-meters, and most preferably greater than about 10 ohm meters. Particularly preferred insulators include, but are not limited to, $SiO_2$, $TiO_2$, $ZrO_2$, porcelain, ceramic, glass, clay, polystyrene, TEFLON, plastics having a resistivity greater than $10^{-3}$ ohm-meters, and other high resistivity plastics, insulating oxides or sulfides of the transition metals in the periodic table of elements, and the like.

The electrodes are conveniently formed from essentially any conductive material. Preferred conductive materials have resistivities of less than about $10^{-3}$ ohm-meters, preferably less than about $10^{-4}$ ohm meters, more preferably less than about $10^{-6}$ ohm meters, and most preferably less than about $10^{-7}$ ohm meters. In preferred embodiments, the electrodes are formed from materials that include, but are not limited to ruthenium, osmium, cobalt, rhodium, rubidium, lithium, sodium, potassium, vanadium, cesium, beryllium, magnesium, calcium, chromium, molybdenum, silicon, germanium, aluminum, iridium, nickel, palladium, platinum, iron, copper, titanium, tungsten, silver, gold, zinc, cadmium, indium tin oxide, cabon or carbon nanotubes, and alloys or compounds of these materials.

II. Sensor Element Arrays

Various embodiments of this invention can utilize a single sensor element. However, in preferred embodiments, a plurality of sensor elements are present, optionally forming an array of sensor elements. As used herein, an array of sensor elements refers to a plurality of sensor elements aggregated on a common substrate and/or that share one or more common electrical connections.

Figure 4A:
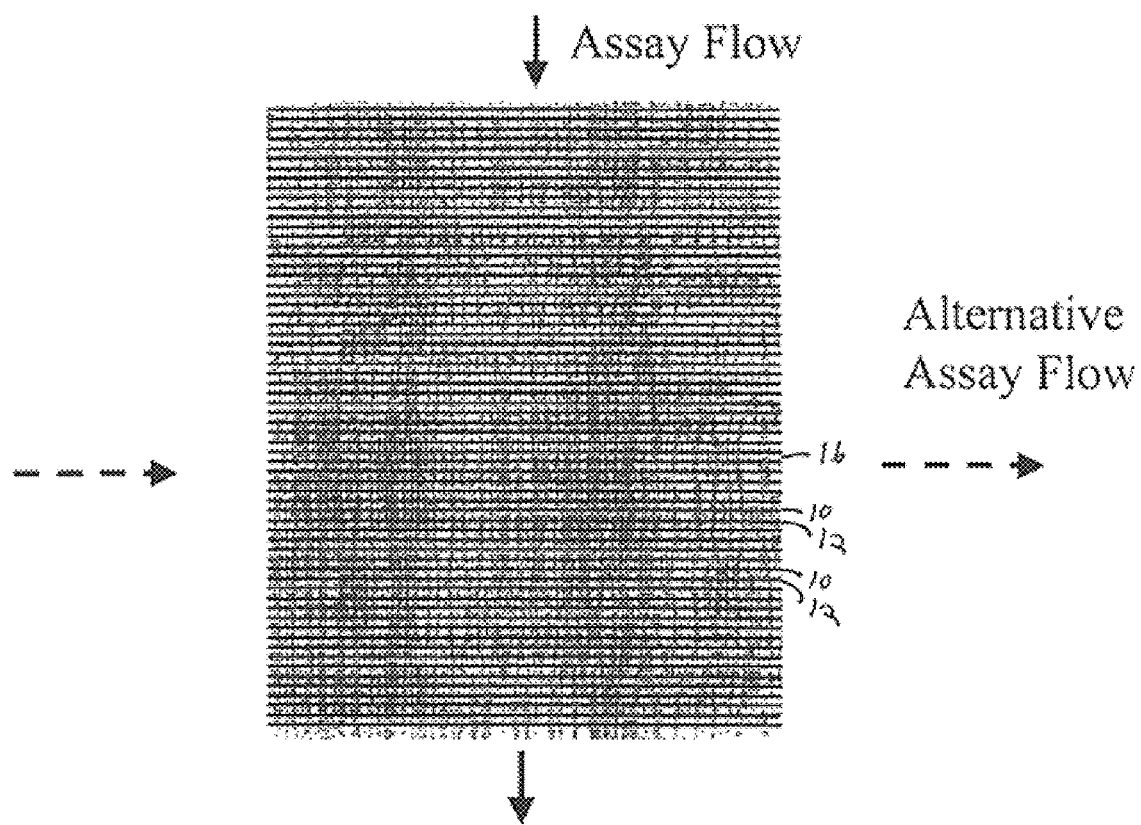
FIGS. 4A and 4B illustrate a simple planar sensor array according to this invention.
Figure 4B:
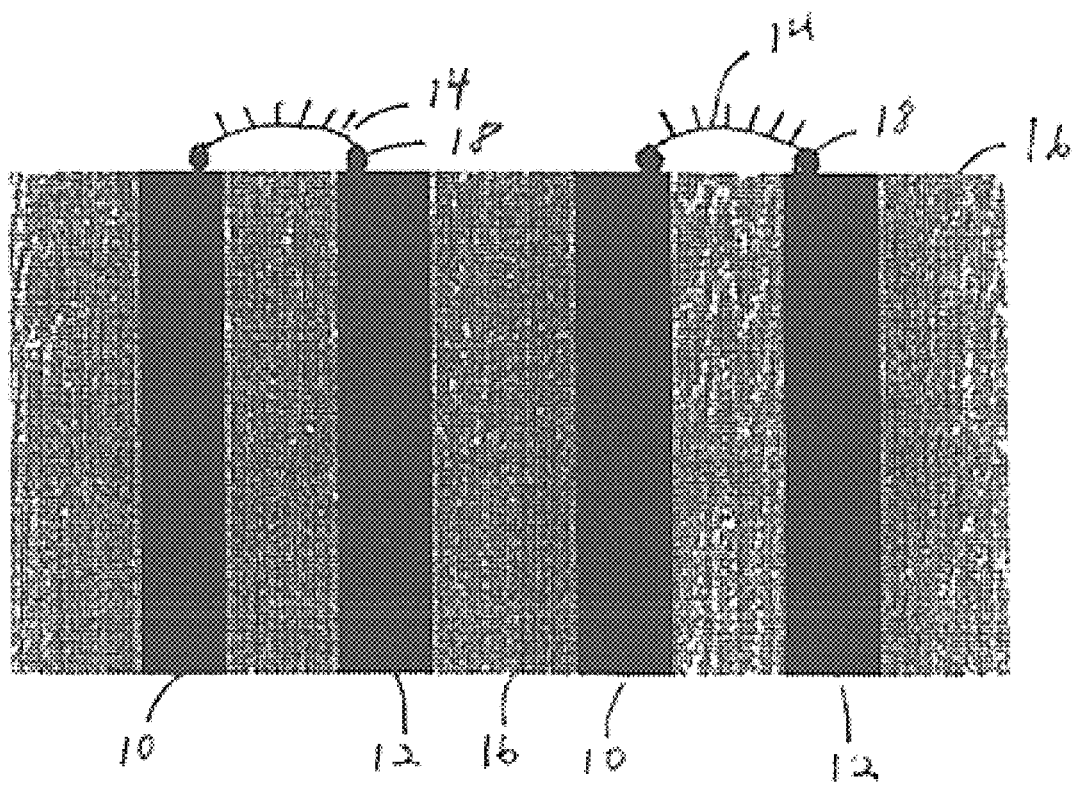
Figure 5:
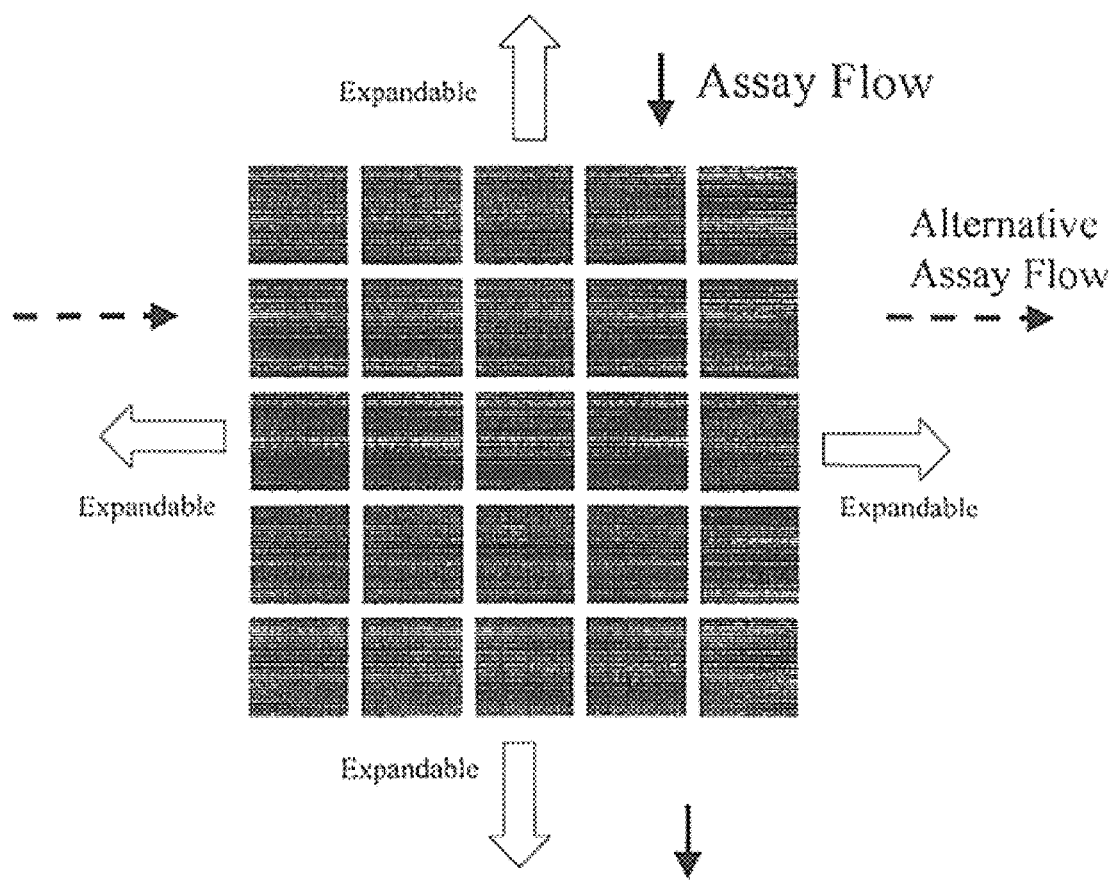
FIG. 5 illustrates an aggregation of sensor arrays according to this invention.

The sensor element arrays can take essentially any conformation that is convenient to the intended application. Thus, in certain embodiments, the sensor element arrays can comprise planar arrays of sensor elements (see, e.g., FIGS. 4A and 4B) and/or aggregations of such arrays (see, e.g., FIG. 5).

The sensor element arrays are not limited to planar arrays. Virtually any configuration can be obtained. Thus, for example, sensor elements or arrays thereof can be placed on one or more walls of a capillary, channel, or microchannel, on one or more walls or floor of a sample well (e.g. in a multi-well plate such as a microtiter plate), on one or more surfaces of a sensor probe (e.g. an insertable or implantable sensor), and the like. In certain embodiments, the sensor arrays can be stacked to provide three-dimensional arrays.

Figure 6A:
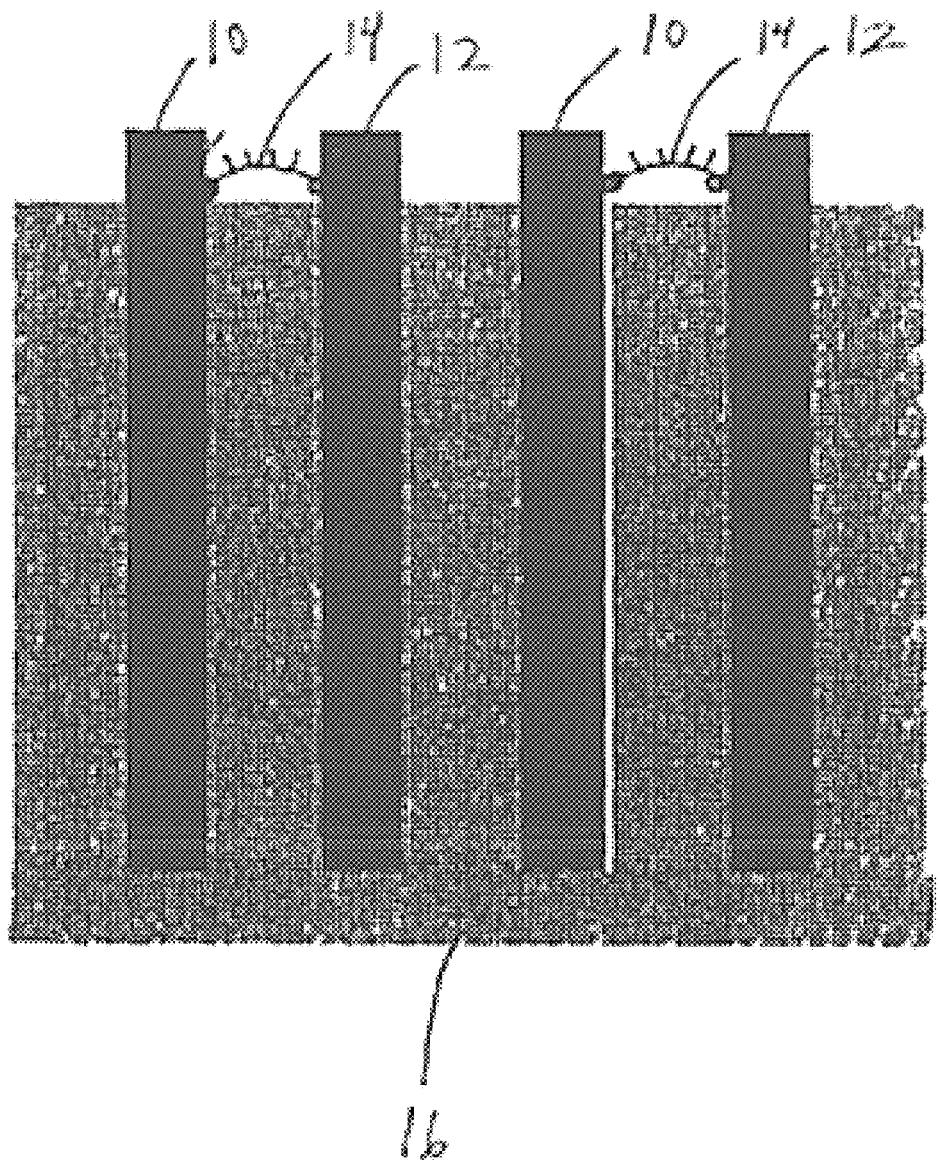
FIGS. 6A through 6C illustrate various sensor embodiments.

Certain preferred configurations are illustrated in FIGS. 4 and 6A through 6C. Thus, for example, FIG. 4B illustrates a flush-faced sensor array. The electrodes and insulators are integrated into a multi-layer material presenting a flush surface. Analyte(s) or solutions containing analytes pass across the surface where the analytes are bound by the binding agent(s) 14. FIG. 6A illustrates an embodiment where the electrodes protrude from the intervening insulator and thereby form one or more channels. The channels are useful for guiding reagents/analytes, and the like, e.g. in various microfluidics devices. The binding agent(s) attached to the electrodes form convenient "detector domains" in such channels. Such devices are readily fabricated by providing a multi-layer material, e.g. as described below, and selectively etching insulator away from the electrodes.

Figure 6C:
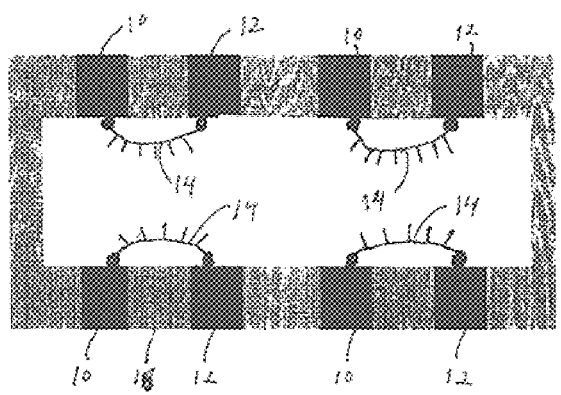
Figure 6B:
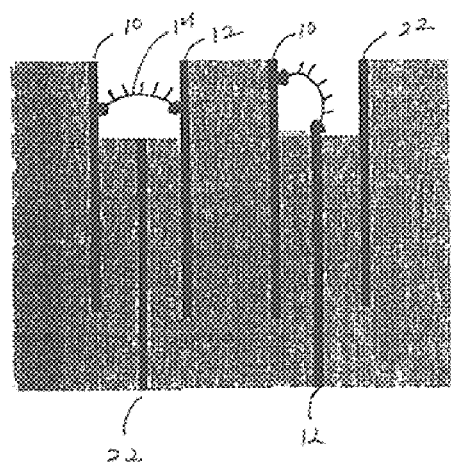

Still another embodiment is illustrated in FIG. 6B. In this embodiment, insulator/support is removed between the electrodes thereby forming channels within the substrate having electrode walls. Optional biasing electrodes 22 are illustrated in FIG. 6B.

FIG. 6C illustrates a close channel or well (cross-section) in which sensor element arrays are present in two walls of the channel.

These configurations are simply illustrative and not intended to be limiting. Using the teaching provided herein, numerous other configurations will be available to one of ordinary skill in the art.

Preferred sensor arrays comprise at least two, preferably at least 10, more preferably at least 100, and most preferably at least 1,000, 10,000, or 1,000,000 sensor elements. The sensor elements can all bear the same biological molecules 14 or various sensor elements can bear different biological molecules and show specificity for different analytes. Thus, in certain embodiments, a single sensor array can detect/quantify two or more, preferably four or more, more preferably 10 or more, still more preferably 100 or more or 1000 or more, and most preferably 10000 or more, 100,000 or more, or even 1,000,000 or more different analytes. In some molecular sensor apparatus in accordance with the present invention, the molecular sensor apparatus comprises $10^2$ to $10^{10}$ electrode pairs.

The electrodes comprising the sensor elements of the array(s) can all be separate, or they can be connected in various combinations. Thus, for example the first electrodes 10 of all of the sensor elements or for a subset of sensor elements can be electrically connected to form a common electrode or "switchably connected to form various electrical connections as desired. Similarly, additional "biasing" electrodes 22 can be connected together or "switchably interconnected.

Numerous methods may be used for addressing the plurality of sensor elements comprising the sensor element arrays of this invention. Several techniques are schematically illustrated in FIGS. 7 through 11. Shown in those figures by way of example are four sensor elements 101, 102, 103, 104 and appropriate instrumentation to read them, which typically is a voltammeter incorporating a digital computer.

Figure 7:
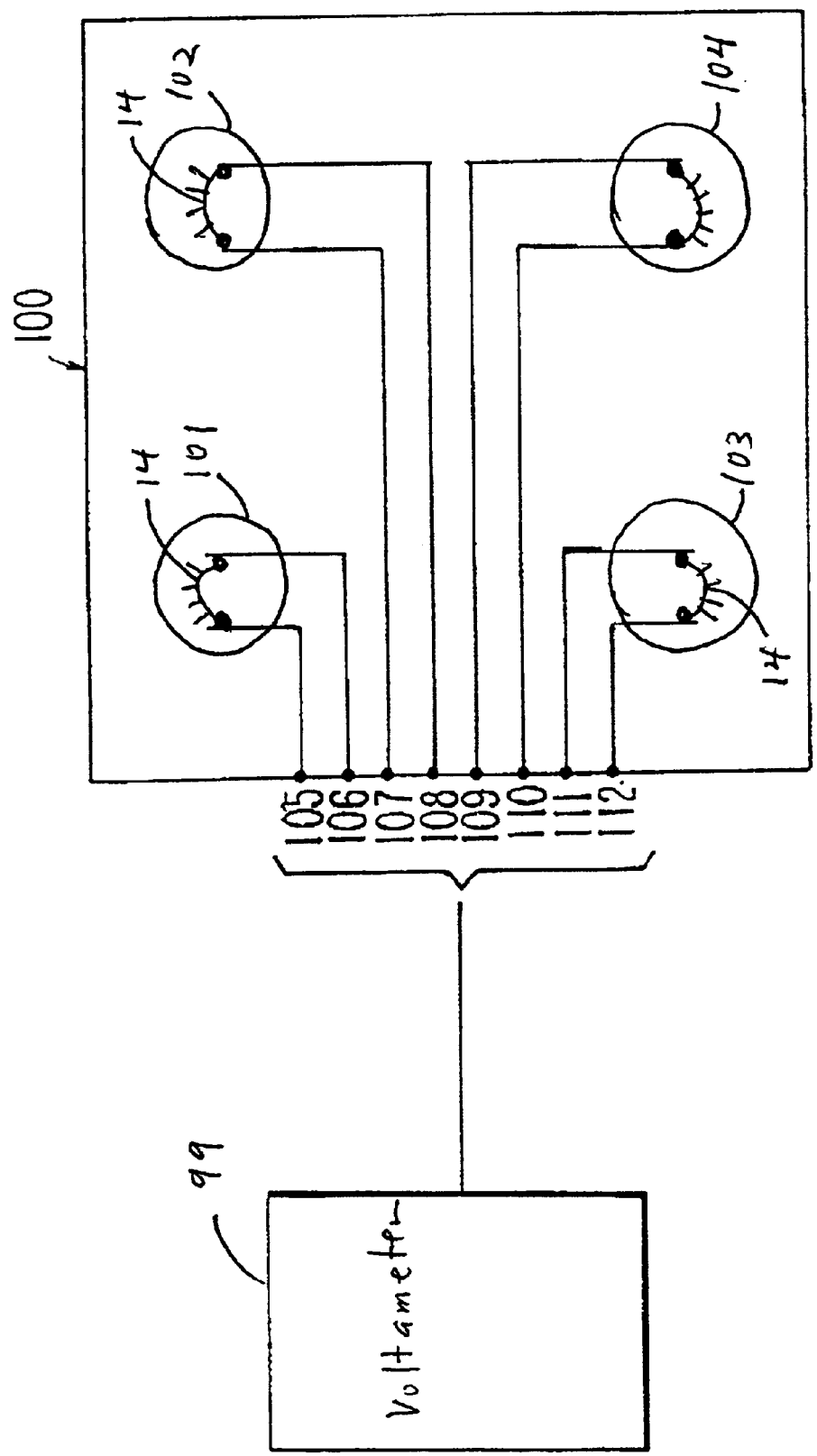
FIG. 7 is a schematic a diagram of a support having an array of electrode pairs (sensor elements) controlled by a computer.

In FIG. 7, each sensor element (electrode pair) pair 101–104 is individually addressed by a pair of lines connected to the voltammeter 99. By way of example, lines 105, 106 access electrode/counterelectrode pair 101. An appropriate voltage may be applied and conductance/resistance measured by the voltammeter at any given time to any one or more of the pairs of lines connected to the various electrode pairs.

Figure 8:
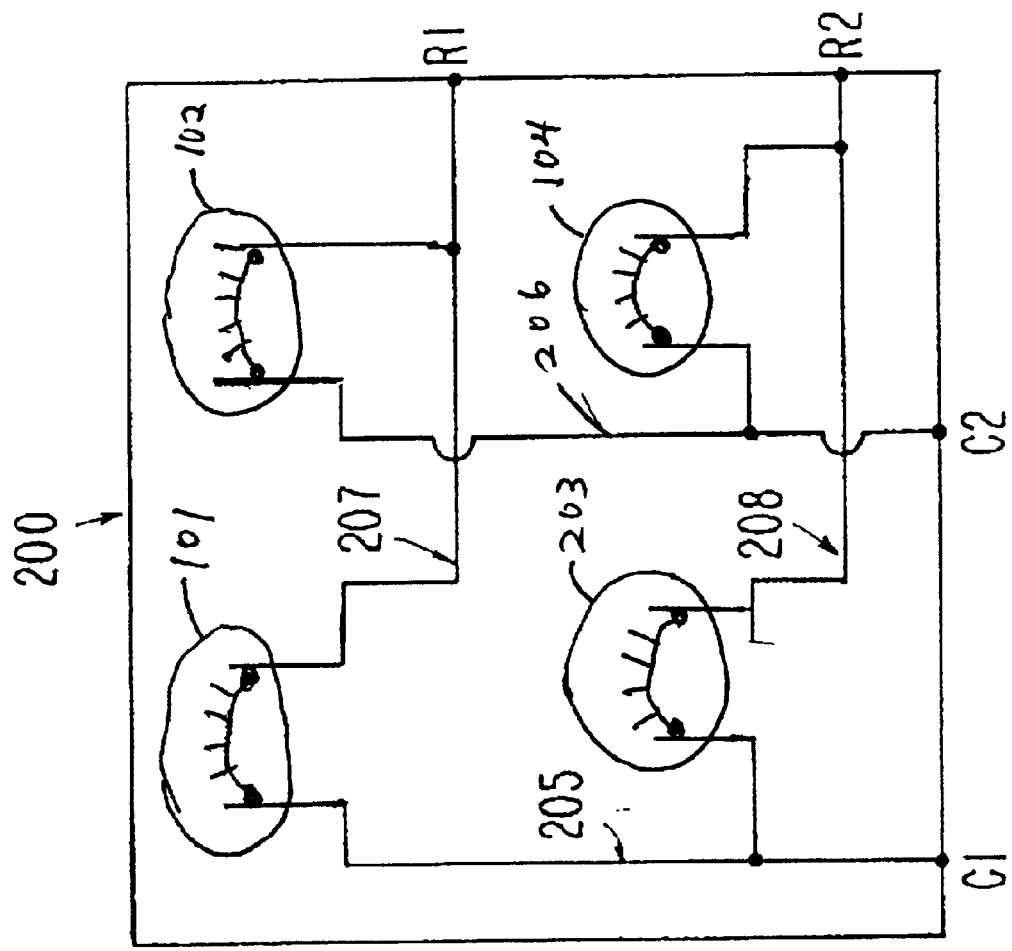
FIG. 8 is a schematic diagram of a support having an array of electrode pairs (sensor elements).

To reduce the number of connections required to address the electrode pairs, alternatives to the direct connection scheme of FIG. 7 are provided. For example, a row-andcolumn accessing scheme is illustrated in FIG. 8 for electrically energizing some or all of the electrodes. In this scheme, one of the electrodes 201, 202 in each column of the plurality of electrode pairs is connected to a common electrical conductor 205 on support 200, and each of the electrodes in each row of the plurality of electrode pairs is connected to conductor 207, 208 on the support 200. Conductors 205, 206 connect to connections C1, C2, respectively, at the edge of support 200 and conductors 207, 208 connect to connections R1, R2, respectively. Each of these connections is then connected by a separate line to the voltammeter. As a result, in the configuration of FIG. 8, the number of required connections and signal lines from the voltammeter has been reduced from 8 to 4.

Figure 9:
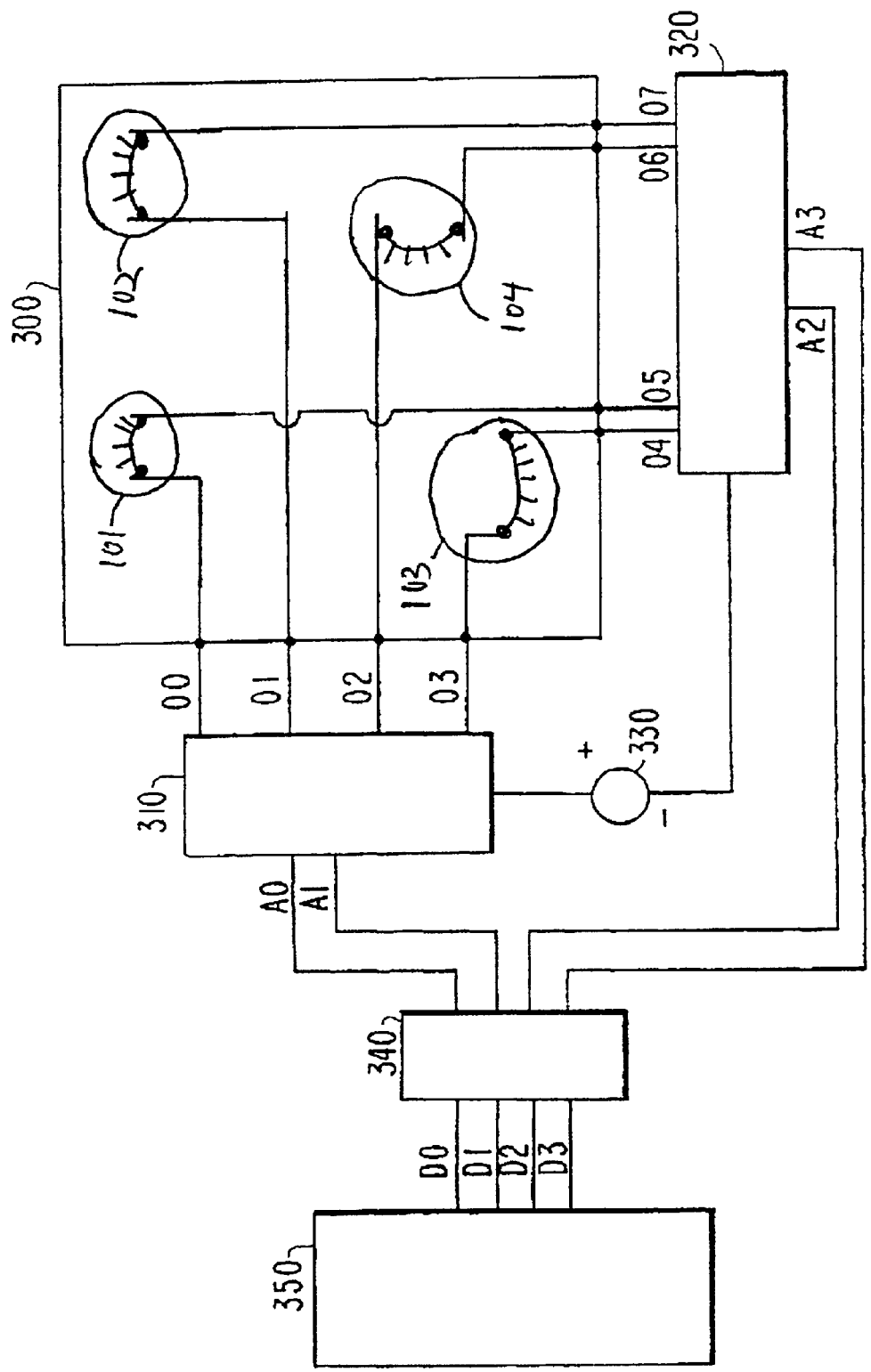
FIG. 9 is a schematic diagram of a support having an array of electrode pairs and computer system for controlling the energization of each electrode pair (sensor element).

To enable rapid and sequential energizing/reading of each electrode pair, a computer controlled switching device is beneficial. The configuration of FIG. 9 shows a plurality of first electrodes connected to a first multiplexer 310. A plurality of second electrodes are connected to a second multiplexer 320. The first multiplexer is also connected to a first pole of a voltage source/voltammeter 330 that typically supplies a time varying electrical potential for cyclic voltammeter described herein. The second multiplexer is also connected to a second pole of the voltage source/voltammeter. Using addressing lines A0–A3 electrically connected to each of the multiplexers and connected to latch 340, a computer processor 350 can direct the multiplexers to selectively connect any or all of the first electrodes to the first pole of the voltammeter, and any or all of the second electrodes to the second pole of the voltammeter.

Figure 10:
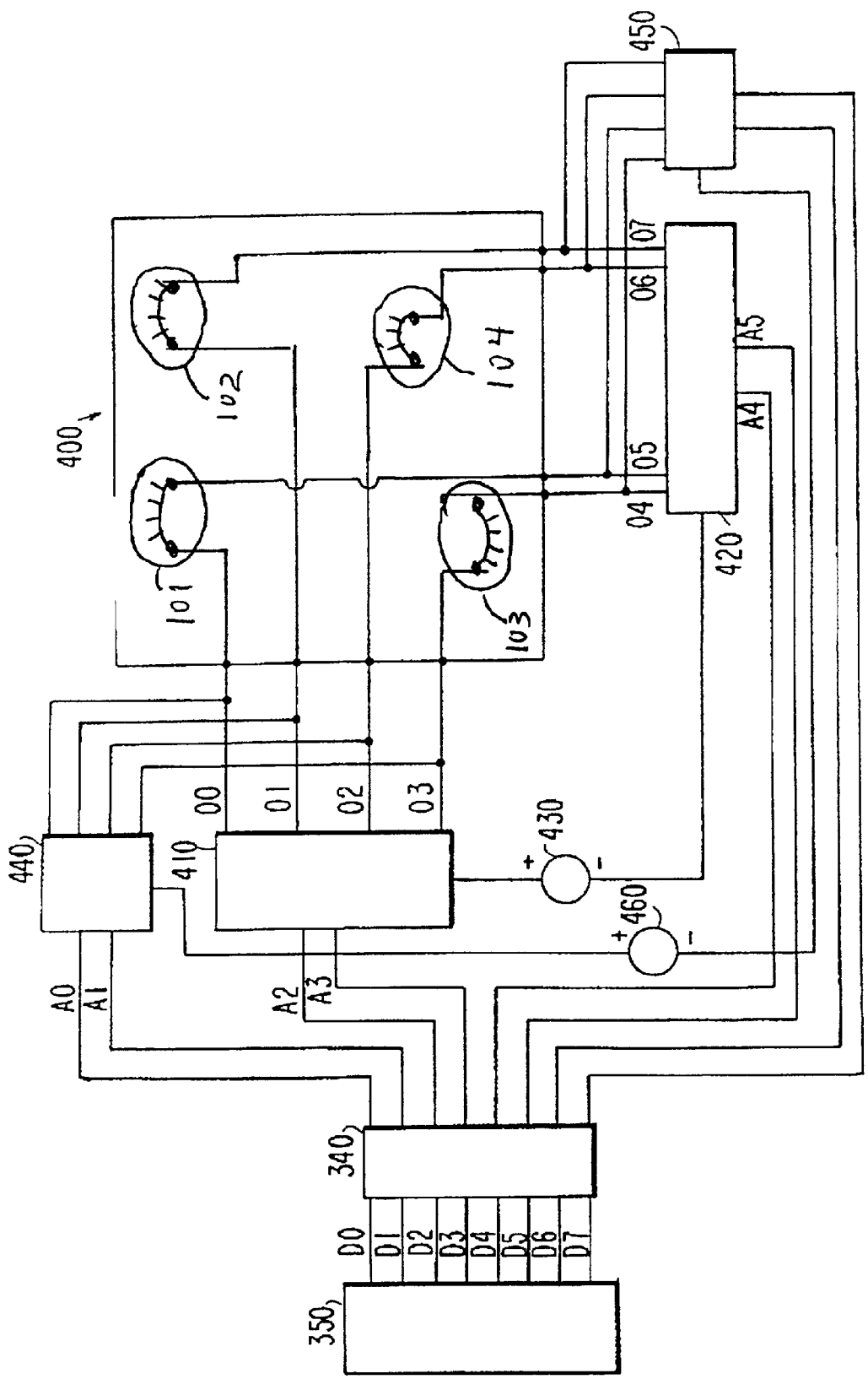
FIG. 10 is a schematic diagram of a support having an array of electrode pairs and a computer system with a plurality of voltage sources and multiplexers for controlling the energization of each electrode pair (sensor element).

As shown in FIG. 10, a plurality of voltage sources are connected through separate sets of multiplexers to each of the electrodes. If a first electrical potential or range of electrical potentials is required at a particular electrode pair, the multiplexers 410, 420 associated with the voltage source 430 providing that potential are addressed by the computer processor 350, typically through a latch 340, thereby connecting that particular voltage source to the electrode pair in question. If a different electrical potential or range of electrical potentials is required for another electrode pair, the multiplexers 440, 450 associated with that different voltage source 460 are addressed by the computer processor, thereby connecting that voltage source through the associated multiplexers 440, 450 to the electrode pair.

If the electrode array in this embodiment has at least a portion of the electrode pairs independently driveable, as shown in FIG. 8 or FIG. 9, for example, one electrode pair can be driven by one voltage source/voltammeter while another electrode pair is simultaneously driven with another voltage source/voltammeter. Alternatively, the two voltage sources of FIG. 10 can be replaced with a single voltage source/voltammeter connected to both sets of multiplexers in parallel, allowing two electrode pairs to be driven from the same voltage source.

Figure 11:
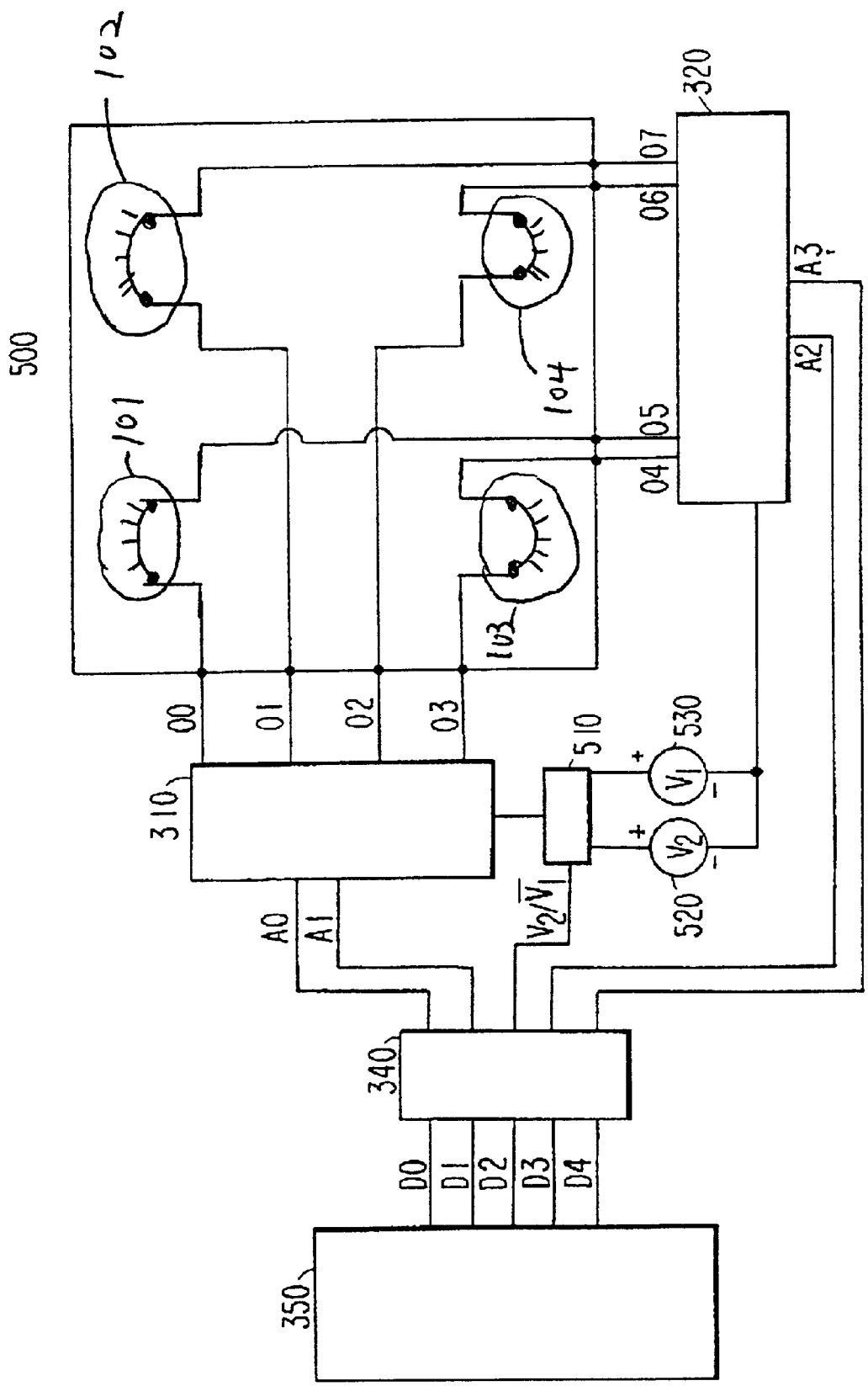
FIG. 11 is a diagram of a support having an array of electrode pairs and a computer system with a plurality of switched voltage sources for controlling the energization of each electrode pair (sensor element).

Instead of a duplicate set of multiplexers for each voltage source as shown in FIG. 10, a plurality of voltage sources/voltammeters 520, 530 can be provided as shown in FIG. 11. These voltage sources can be connected through a computer controlled electrical switch 510 or switches to a single set of multiplexers 310, 320. As shown in FIG. 11, the computer would direct switch 510 to connect a particular voltage source/voltammeter to the multiplexers, and would also direct the multiplexers (by signaling their address lines A0–A3) to connect the selected voltage source to the particular electrode pair desired.

Alternatively, the electrical potential applied to each of the electrode pairs in any embodiment can be varied. This is of particular benefit when a cassette having a plurality of different sensor elements is used. Such a cassette may require a different range of applied electrical potential at different sensor elements. Several different embodiments capable of varying the electrical potential applied to each electrode are contemplated.

Advantageously, a computer controlled voltage source/voltammeter may be used. A computer controlled voltage source/amperometer is one that can be addressed by a computer to select a particular electrical potential/waveform to be supplied. Alternatively it can be programmed to sequentially apply a particular range of electrical potentials over a predetermined time. In such a system, address lines electrically connected to the computer and the voltage source allow the computer to program the voltage source to produce the particular electrical potential to be applied to the electrode pair to be energized.

Additional methods for addressing the plurality of electrode pairs may also be used. For example, a plurality of reference electrodes may be placed in proximity to each of the plurality of electrode pairs in order to sense the voltage applied thereto. In this way, additional control of the voltage waveform may be maintained.

While the foregoing discussion was with reference to voltage sources/amperometers, other means of driving/reading the sensor elements can be substituted therefor. Such means include, but are not limited to amperometers, coulometers, and the like.

III. Sensor Molecules and Target Analytes

A) Preferred Sensor Molecules and Target Analytes

A wide variety of binding agents (binding reagents) 14 can be used in the devices of this invention and the analytes that can be detected using such binding agents are virtually limitless. The binding agents specifically bind to at least one analyte (ligand) of interest. The binding reagents can be selected from among any molecules known in the art to be capable of, or putatively capable of, specifically binding an analyte of interest.

Preferred analytes of interest include, but are not limited to a whole cell, a subcellular particle, virus, prion, viroid, nucleic acid, protein, antigen, lipoprotein, lipopolysaccharide, lipid, glycoprotein, carbohydrate moiety, cellulose derivative, antibody or fragment thereof, peptide, hormone, pharmacological agent, cell or cellular components, organic compounds, non-biological polymer, synthetic organic molecule, organo-metallic compounds, or an inorganic molecule present in the sample.

The sample can be derived from, for example, a solid, emulsion, suspension, liquid or gas. Furthermore, the sample may be derived from, for example, body fluids or tissues, water, food, blood, serum, plasma, urine, feces, tissue, saliva, oils, organic solvents, earth, water, air, or food products. The sample may comprise a reducing agent or an oxidizing agent, solubilizer, diluent, preservative, or other suitable agents.

Suitable binding agents (biological molecules) 14 include, but are not limited to receptors, ligands for receptors, antibodies or binding portions thereof (e.g., Fab, (Fab)'$_2$), proteins or fragments thereof, nucleic acids, oligonucleotides, glycoproteins, polysaccharides, antigens, epitopes, carbohydrate moieties, enzymes, enzyme substrates, lectins, protein A, protein G, organic compounds, organometallic compounds, lipids, fatty acids, lipopolysaccharides, peptides, cellular metabolites, hormones, pharmacological agents, tranquilizers, barbiturates, alkaloids, steroids, vitamins, amino acids, sugars, nonbiological polymers, biotin, avidin, streptavidin, organic linking compounds such as polymer resins, lipoproteins, cytokines, lymphokines, hormones, synthetic polymers, organic and inorganic molecules, etc.

It will be apparent from the foregoing that the binding agent (e.g., biological molecule) 14 and its target analyte 20 can exist as a pair of "binding partners", e.g. a ligand and its cognate receptor, an antibody and its epitope, etc. Thus, a biological "binding partner" or a member of a "binding pair" refers to a molecule or composition that specifically binds other molecules to form a binding complex such as antibody-antigen, lectin-carbohydrate, nucleic acid-nucleic acid, biotin-avidin, etc.

The term "specifically binds", as used herein, when referring to a binding agent (e.g., protein, nucleic acid, antibody, etc.), refers to a binding reaction that is determinative of the presence binding agent heterogeneous population of proteins and other biologics. Thus, under designated conditions (e.g. immunoassay conditions in the case of an antibody, or stringent hybridization conditions in the case of a nucleic acid), the specified ligand or antibody binds to its particular "target" (e.g. a protein or nucleic acid) and does not bind in a significant amount to other molecules.

Figure 13:
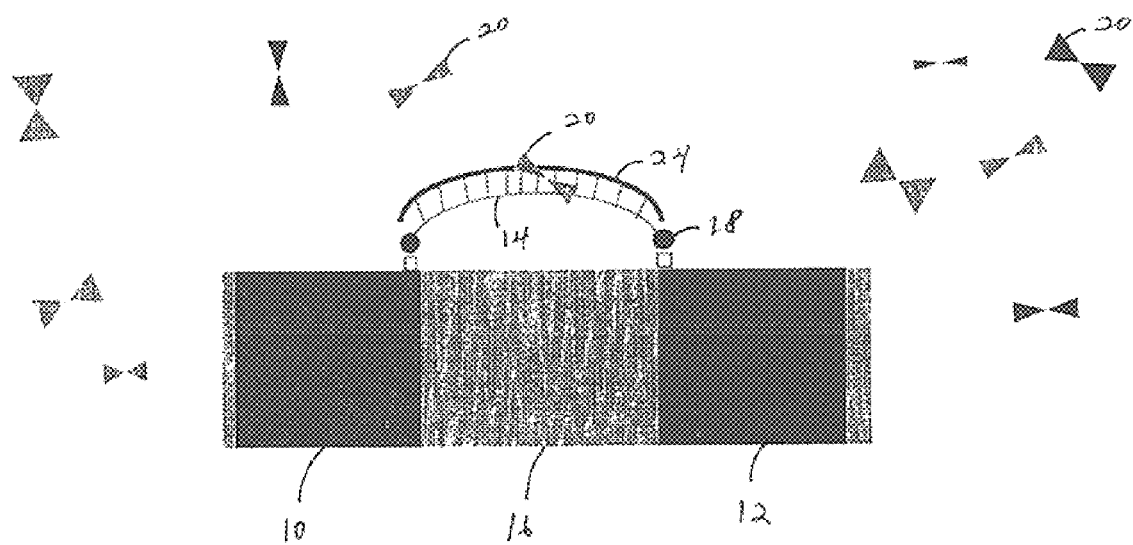
FIG. 13 illustrates the use of a biosensor to detect protein/DNA interactions. A biosensor comprising a nucleic acid 14 is hybridized to a second nucleic acid 24 to form a double-stranded nucleic acid spanning two electrodes. Binding of a protein analyte 20 (e.g. DNA binding protein) to the nucleic acid changes conductance of the nucleic acid thereby producing a detectable signal.

The binding partner(s) used in this invention are selected based upon the targets that are to be identified/quantified. Thus, for example, where the target is a nucleic acid the binding partner is preferably a nucleic acid or a nucleic acid binding protein or protein complex (see, e.g, FIG. 13). Where the target is a protein, the binding partner is preferably a receptor, a ligand, or an antibody that specifically binds that protein. Where the target is a sugar or glycoprotein, the binding partner is preferably a lectin, and so forth.

B) Preparation Of Binding Partners (Capture Agents)

Methods of synthesizing or isolating suitable binding agents are well known to those of skill in the art as explained below.

1) Nucleic Acids

Nucleic acids for use as binding agents 14 in this invention can be produced or isolated according to any of a number of methods well known to those of skill in the art. In one embodiment, the nucleic acid can be an isolated naturally occurring nucleic acid (e.g., genomic DNA, cDNA, mRNA, etc.). Methods of isolating naturally occurring nucleic acids are well known to those of skill in the art (see, e.g., Sambrook et al. (1989) *Molecular Cloning—A Laboratory Manual* (2nd Ed.), Vol. 1–3, Cold Spring Harbor Laboratory, Cold Spring Harbor, N.Y.).

In a preferred embodiment, the nucleic acid is created de novo, e.g. through chemical synthesis, e.g., according to the solid phase phosphoramidite triester method described by Beaucage and Caruthers (1981), *Tetrahedron Letts.,* 22(20): 1859–1862, e.g., using an automated synthesizer, as described in Needham-VanDevanter et al. (1984) *Nucleic Acids Res.*, 12: 6159–6168. Purification of oligonucleotides, where necessary, is typically performed by either native acrylamide gel electrophoresis or by anion-exchange HPLC as described in Pearson and Regnier (1983) *J. Chrom.* 255: 137–149. The sequence of the synthetic oligonucleotides can be verified using the chemical degradation method of Maxam and Gilbert (1980) in Grossman and Moldave (eds.) Academic Press, New York, *Meth. Enzymol.* 65: 499–560.

2) Antibodies/antibody Fragments

Antibodies or antibody fragments for use in sensor elements of this invention can be produces by a number of methods well known to those of skill in the art (see, e.g., Harlow & Lane (1988) *Antibodies: A Laboratory Manual*, Cold Spring Harbor Laboratory, and Asai (1993) *Methods in Cell Biology Vol. 37: Antibodies in Cell Biology*, Academic Press, Inc. N.Y.). In one approach, the antibodies are produced by immunizing an animal (e.g. a rabbit) with an immunogen containing the epitope it is desired to recognize/capture. A number of immunogens may be used to produce specifically reactive antibodies. Recombinant protein is the preferred immunogen for the production of monoclonal or polyclonal antibodies. Naturally occurring protein may also be used either in pure or impure form. Synthetic peptides made as well using standard peptide synthesis chemistry (see, e.g., Barany and Merrifield, *Solid-Phase Peptide Synthesis*; pp. 3–284 in *The Peptides: Analysis, Synthesis, Biology. Vol. 2: Special Methods in Peptide Synthesis, Part A.,* Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.)

Methods of production of polyclonal antibodies are known to those of skill in the art. In brief, an immunogen is mixed with an adjuvant and animals are immunized. The animal's immune response to the immunogen preparation is monitored by taking test bleeds and determining the titer of reactivity to the immunogen. When appropriately high titers of antibody to the immunogen are obtained, blood is collected from the animal and antisera are prepared. Further fractionation of the antisera to enrich for antibodies reactive to the immunogen can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein (1976) *Eur. J. Immunol.* 6: 511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science*, 246:1275–1281.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment from a library of greater than $10^{10}$ nonbinding clones. To express antibody fragments on the surface of phage (phage display), an antibody fragment gene is inserted into the gene encoding a phage surface protein (pHIII) and the antibody fragment-pIII fusion protein is displayed on the phage surface (McCafferty et al. (1990) *Nature*, 348: 552–554; Hoogenboom et al. (1991) *Nucleic Acids Res.* 19: 4133–4137).

Since the antibody fragments on the surface of the phage are functional, phage bearing antigen binding antibody fragments can be separated from non-binding phage by antigen affinity chromatography (McCafferty et al. (1990) *Nature*, 348: 552–554). Depending on the affinity of the antibody fragment, enrichment factors of 20 fold–1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) *Nature*, 348: 552–554). Thus even when enrichments are low (Marks et al. (1991) *J. Mol. Biol.* 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) *J. Mol. Biol.* 222: 581–597). In one embodiment natural $V_H$ and $V_L$ repertoires present in human peripheral blood lymphocytes are were isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al (1991) *J. Mol. Biol.* 222: 581–597; Marks et al. (1993). *Bio/Technology*. 10: 779–783; Griffiths et al. (1993) *EMBO J*. 12: 725–734; Clackson et al. (1991) *Nature*. 352: 624–628). Antibodies have been produced against self proteins, including human thyroglobulin, immunoglobulin, tumor necrosis factor and CEA (Griffiths et al. (1993) *EMBO J*. 12: 725–734). It is also possible to isolate antibodies against cell surface antigens by selecting directly on intact cells. The antibody fragments are highly specific for the antigen used for selection and have affinities in the 1:M to 100 nM range (Marks et al. (1991) *J. Mol. Biol.* 222: 581–597; Griffiths et al. (1993) *EMBO J*. 12: 725–734). Larger phage antibody libraries result in the isolation of more antibodies of higher binding affinity to a greater proportion of antigens.

3) Binding Proteins

In one embodiment, the binding partner (capture agent) can be a binding protein. Suitable binding proteins include, but are not limited to receptors (e.g. cell surface receptors), receptor ligands, cytokines, transcription factors and other nucleic acid binding proteins, growth factors, etc.

The protein can be isolated from natural sources, mutagenized from isolated proteins or synthesized de novo. Means of isolating naturally occurring proteins are well known to those of skill in the art. Such methods include but are not limited to well known protein purification methods including ammonium sulfate precipitation, affinity columns, column chromatography, gel electrophoresis and the like (see, generally, R. Scopes, (1982). *Protein Purification*, Springer-Verlag, N.Y.; Deutscher (1990) *Methods in Enzymology Vol.* 182: *Guide to Protein Purification*, Academic Press, Inc. N.Y.).

Where the protein binds a target reversibly, affinity columns bearing the target can be used to affinity purify the protein. Alternatively the protein can be recombinantly expressed with a HIS-Tag and purified using $Ni^{2+}$/NTA chromatography.

In another embodiment, the protein can be chemically synthesized using standard chemical peptide synthesis techniques. Where the desired subsequences are relatively short the molecule may be synthesized as a single contiguous polypeptide. Where larger molecules are desired, subsequences can be synthesized separately (in one or more units) and then fused by condensation of the amino terminus of one molecule with the carboxyl terminius of the other molecule thereby forming a peptide bond. This is typically accomplished using the same chemistry (e.g., Fmoc, Tboc) used to couple single amino acids in commercial peptide synthesizers.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield (1962) *Solid-Phase Peptide Synthesis*; pp. 3–284 in *The Peptides: Analysis, Synthesis, Biology. Vol. 2: Special Methods in Peptide Synthesis, Part A.*, Merrifield et al. (1963) *J. Am. Chem. Soc.*, 85: 2149–2156, and Stewart et al. (1984) *Solid Phase Peptide Synthesis*, 2nd ed. Pierce Chem. Co., Rockford, Ill.

In a preferred embodiment, the protein can also be synthesized using recombinant DNA methodology. Generally this involves creating a DNA sequence that encodes the binding protein, placing the DNA in an expression cassette under the control of a particular promoter, expressing the protein in a host, isolating the expressed protein and, if required, renaturing the protein.

DNA encoding binding proteins or subsequences of this invention can be prepared by any suitable method as described above, including, for example, cloning and restriction of appropriate sequences or direct chemical synthesis by methods such as the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.* 22: 1859–1862; and the solid support method of U.S. Pat. No. 4,458,066.

The nucleic acid sequences encoding the desired binding protein(s) may be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant binding proteins can be purified according lo standard procedures of the art as described above.

4) Sugars and Carbohydrates

Other binding agents suitable for sensor elements of this invention include, but are not limited to, sugars and carbohydrates. Sugars and carbohydrates can be isolated from natural sources, enzymatically synthesized or chemically synthesized. A route to production of specific oligosaccharide structures is through the use of the enzymes which make them in vivo; the glycosyltransferases. Such enzymes can be used as regio- and stereoselective catalysts for the in vitro synthesis of oligosaccharides (Ichikawa et al. (1992) *Anal.*

*Biochem.* 202: 215–238). Sialyltransferase can be used in combination with additional glycosyltransferases. For example, one can use a combination of sialyltransferase and galactosyltransferases. A number of methods of using glycosyltransferases to synthesize desired oligosaccharide structures are known. Exemplary methods are described, for instance, WO 96/32491, Ito et al. (1993) *Pure Appl. Chem.* 65:753, and U.S. Pat. Nos. 5,352,670, 5,374,541, and 5,545,553. The enzymes and substrates can be combined in an initial reaction mixture, or alternatively, the enzymes and reagents for a second glycosyltransferase cycle can be added to the reaction medium once the first glycosyltransferase cycle has neared completion. By conducting two glycosyltransferase cycles in sequence in a single vessel, overall yields are improved over procedures in which an intermediate species is isolated.

Methods of chemical synthesis are described by Zhang et al. (1999) *J. Am. Chem. Soc.*, 121(4): 734–753. Briefly, in this approach, a set of sugar-based building blocks is created with each block preloaded with different protecting groups. The building blocks are ranked by reactivity of each protecting group. A computer program then determines exactly which building blocks must be added to the reaction so that the sequences of reactions from fastest to slowest produces the desired compound.

IV. Assembling a Sensor

The biosensors of this invention can be assembled using methods well known to those of skill in the art. In general two or more electrodes are provided having an interelectrode spacing sufficiently small that the biomolecule/target analyte complex is capable of carrying charge from one electrode to the other. The electrode(s) are then contacted with the biomolecule(s) 14 in a manner that facilitates the electrical coupling and physical attachment of the biomolecule(s) to one or both electrodes (depending on device configuration). The electrode(s) and/or the biomolecules can be derivatized so that the molecules self assemble/attach to the electrode.

A) Providing Two or More Electrodes

Methods of providing electrodes closely positioned with respect to each other are well known to those of skill in the art. Thus, for example, electrodes can be precisely positioned using micromanipulators, atomic force microscope (AFM) or STM tips, and the like. In preferred embodiments, the plurality of electrodes (optional counter electrodes) and the like are typically placed in registered proximity to one another by mechanical means, e.g., by using guide posts, alignment pins, guide edges, and the like. Other systems using electrical or magnetic registration means are also available.

In particularly preferred embodiments, the electrodes are fabricated/positioned using micromachining processes (e.g. photolithography) well known in the solid state electronics industry. Commonly, microdevices are constructed from semiconductor material substrates such as crystalline silicon, widely available in the form of a semiconductor wafer used to produce integrated circuits, or from glass. Because of the commonality of material(s), fabrication of microdevices from a semiconductor wafer substrate can take advantage of the extensive experience in both surface and bulk etching techniques developed by the semiconductor processing industry for integrated circuit (IC) production.

Surface etching, used in IC production for defining thin surface patterns in a semiconductor wafer, can be modified to allow for sacrificial undercut etching of thin layers of semiconductor materials to create movable elements. Bulk etching, typically used in IC production when deep trenches are formed in a wafer using anisotropic etch processes, can be used to precisely machine edges or trenches in microdevices. Both surface and bulk etching of wafers can proceed with "wet processing", using chemicals such as potassium hydroxide in solution to remove non-masked material from a wafer. For microdevice construction, it is even possible to employ anisotropic wet processing techniques that rely on differential crystallographic orientations of materials, or the use of electrochemical etch stops, to define various channel elements.

Another etch processing technique that allows great microdevice design freedom is commonly known as "dry etch processing". This processing technique is particularly suitable for anistropic etching of fine structures. Dry etch processing encompasses many gas or plasma phase etching techniques ranging from highly anisotropic sputtering processes that bombard a wafer with high energy atoms or ions to displace wafer atoms into vapor phase (e.g. ion beam milling), to somewhat isotropic low energy plasma techniques that direct a plasma, stream containing chemically reactive ions against a wafer to induce formation of volatile reaction products.

Intermediate between high energy sputtering techniques and low energy plasma techniques is a particularly useful dry etch process known as reactive ion etching. Reactive ion etching involves directing an ion containing plasma stream against a semiconductor, or other, wafer for simultaneous sputtering and plasma etching. Reactive ion etching retains some of the advantages of anisotropy associated with sputtering, while still providing reactive plasma ions for formation of vapor phase reaction products in response to contacting the reactive plasma. ions with the wafer. In practice, the rate of wafer material removal is greatly enhanced relative to either sputtering techniques or low energy plasma techniques taken alone. Reactive ion etching therefore has the potential to be a superior etching process for construction of microdevices, with relatively high anistropic etching rates being sustainable. The micromachining techniques described above, as well as many others, arc well known to those of skill in the art (see, e.g., Choudhury (1997) *The Handbook of Microlithography, Micromachining, and Microfabrication*, Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

In certain embodiments, the electrodes, particularly electrode arrays of this invention are formed as multilayer materials, e.g. alternating layers of dialetric and conductor. When etched, cut, or otherwise fractured, the edge of such multilayer materials affords electrodes separated by dialectric/insulator at extremely high density (close spacing).

Multilayer materials are widely known in the materials community for scientific study and physics applications and their use has been demonstrated widely (see, e.g., U.S. Pat. Nos. 4,673,623, 4,870,648, 4,915,463 and the like).

Such electrode arrays are readily fabricated using sputtering techniques (see, e.g. U.S. Pat. Nos. 5,203,977, 5,486, 277, 5,742,471, and the like). Sputtering is a vacuum coating process where an electrically isolated cathode is mounted in a chamber that can be evacuated and partially filled with an inert gas. If the cathode material is an electrical conductor, a direct-current high-voltage power supply is used to apply the high voltage potential. If the cathode is an electrical insulator, the polarity of the electrodes is reversed at very high frequencies to prevent the formation of a positive charge on the cathode that would stop the ion bombardment process. Since the electrode polarity is reversed at a radio frequency, this process is referred to as RF-sputtering.

Magnetron sputtering is a more effective form than diode sputtering that uses a magnetic field to trap electrons in a region near the target surface creating a higher probability of ionizing a gas atom. The high density of ions created near the target surface causes material to be removed many times faster than in diode sputtering. The magnetron effect is created by an array of permanent magnets included within the cathode assembly that produce a magnetic field normal to the electric field. While other sputtering techniques may be used, in particularly preferred embodiments, magnetron sputtering, e.g. as described in U.S. Pat. No. 5,486,277, is used to provide the electrode arrays of this invention.

B) Attachment of Biomolecules to Electrodes

The binding agents (e.g. biomolecules) are attached to the electrodes using methods well known to those of skill in the art. Typically the electrode(s) and/or the binding agent(s) are derivatized (functionalized) with reactive moieties (e.g. linkers) that facilitate attachment of the electrode to the binding agent. Thus, for example in certain embodiments, the binding agent bears a reactive linker (e.g. an aliphatic thiol linker) that reacts with the electrode surface or with a functional group attached thereto, and/or the electrode is derivatized with a linker that binds to the biomolecule.

The linker can be electrically conductive or it can be short enough that electrons can pass directly or indirectly between the electrode and the biological molecule 14.

The manner of linking a wide variety of compounds to various surfaces is well known and is amply illustrated in the literature. Means of coupling the biological molecules 14 will be recognized by those of skill in the art. The linkage can be covalent, or by ionic or other non-covalent interactions. The surface and/or the molecule(s) may be specifically derivatized to provide convenient linking groups (e.g. sulfur, hydroxyl, amino, etc.).

The linker(s) can be provided as a part of a derivatized binding agent or they can be provided separately. Linkers, when not joined to the molecules to be linked are often either hetero- or homo-bifunctional molecules that contain two or more reactive sites that may each form a covalent bond with the respective binding partner (i.e. electrode surface or biological molecule). When provided as a component the biological molecule, or attached to the electrode, the linkers are preferably spacers having one or more reactive sites suitable for bonding to the respective surface or molecule.

Linkers suitable for joining molecules are well known to those of skill in the art and include, but are not limited to any of a variety of, a straight or branched chain carbon linker, or a heterocyclic carbon linker, amino acid or peptide linkers, and the like. Particularly preferred linkers include, but are not limited to 4,4'-diphenylethyne, 4,4'-diphenylbutadiyne 4,4'-biphenyl, 1,4-phenylene, 4,4'-stilbene, 1,4-bicyclooctane, 4,4'-azobenzene, 4,4'-benzylideneaniline, and 4,4"-terphenyl, oligophenylene vinylene, and the like (see, e.g., U.S. Pat. No. 6,208,553).

A wide variety of such linkers comprising surface binding groups are know to those of skill in the art and are often used to produce self-assembling monolayers. Such groups include, but are not limited to thiols (e.g. alkanethiols) (which bind gold and other metals), alkyltrichlorosilane (e.g., which bind silicon/silicon dioxide), alkane carboxylic acids (e.g., which bind aluminum oxides), derivatives of ethylene glycol, as well as combinations thereof (see, e.g., Ferguson et al. (1993) *Macromolecules* 26(22): 5870–5875; Prime et al. (1991) *Science* 252:1164–1167; Bain et al.

(1989) *Angew. Chem.* 101: 522–528; Kumar et al. (1994) *Langmuir* 10: 1498–1511; Laibinis et al. (1989) *Science* 245: 845–847; Pale-Grosdemange et al. (1991) *J. Am. Chem. Soc.*, 113: 12–20, and the like). In particularly preferred embodiments, the biological molecules 14 are attached to metal electrodes using thiol linkers (e.g., alkanethiol linkers).

In certain embodiments, the binding agents are functionalized with a chemical group, or a linker bearing a chemical group, that can be activated by the application of an electrical potential. Such groups are well known to those of skill in the art and include, but are not limited to S-benzyloxycarbonyl derivatives, S-benzyl thioethers, S-phenyl thioethers, S-4-picolyl thioethers, S-2,2,2-trichloroethoxycarbonyl derivatives, S-triphenylmethyl thioethers, and the like. In certain embodiments, the binding agents are functionalized with a chemical group, or a linker bearing a chemical group that can be activated by light of wavelength ranging from 190 nm to 700 nm. Such chemcial groups include, but are not limited to an aryl azide, a flourinated aryl azide, a benzophenone, and (R,S)-1-(3,4-(methylene-dioxy)-6-nitrophenyl)ethyl cholorformate-(MeNPOC), N-((2-pyridyl, ethyl)-4-azido) salicylamide.

In a particularly preferred embodiment the derivatized biological molecule, in solution, is contacted with the electrode(s). A charge is placed on the first electrode 10 to attract the biological molecule thereto. Upon contact with the electrode, the derivatized biological molecule binds to the electrode. The derivatized biological molecule can bear two linkers, one for attachment to the first electrode and one derivatized for attachment to the second electrode. In such embodiments, the second linker can be blocked to prevent reaction with the first electrode. After the biological molecule has been bound to the first molecule the linker is deprotected permitting binding to the second electrode.

Thus, for example to span two electrodes with a biological molecule that is a nucleic acid, the nucleic acid is derivatized with two linkers one protected (blocked) thiol and one deprotected (unblocked) thiol. The first electrode 12 is biased positive to attract the nucleic acid thereto whereby the thiol linker binds to the first electrode. The first electrode 10 is then biased negative and the second electrode 12 is biased positive to attract the free end of the nucleic acid to second electrode. The blocked thiol linker is deprotected leaving that linker free to interact with the second. This results in a nucleic acid spanning gap between the first and the second electrode.

This assembly approach thus uses the device itself, to direct the localization and ultimate attachment of the binding agent. Thus, the devices of this invention are able to electronically self-address each sensor element with a specific binding agent. The device self-assembles itself in the sense that no outside process, mechanism, or equipment is needed to physically direct, position, or place a specific binding agent at a specific location/sensor element/electrode. This self-addressing process is both rapid and specific, and can be carried out in either a serial or parallel manner.

The device can be serially addressed with specific binding agent by maintaining selected sensor element(s)/electrode(s) in a DC mode and at the opposite charge (potential) to that of a specific binding entity. Other sensor elements/electrodes are maintained at the same charge as the specific binding agent. In cases where the binding agent is not in excess of the attachment sites on electrode(s), it is necessary to activate only one other micro-electrode to affect the electrophoretic transport to the specific micro-location. The specific binding agent is rapidly transported (in a few seconds, or preferably less than a second) through the solution, and concentrated directly at the specific electrode where can covalently bonded to the electrode surface.

The parallel process for addressing sensor elements/electrodes simply involve's simultaneously activating a large number (particular group or line) of electrodes so that the same specific binding entity is transported, concentrated, and reacted with more than one specific electrode.

This approach is simply illustrative. Numerous other approaches can be used to attach the biological molecule to the respective electrode(s). Such approaches include, but are not limited to attachment of chemical groups to the surface through the use of photoactivatable chemistries (see, e.g., Sundberg et al. (1995) *J. Am. Chem. Soc.* 117(49):12050–12057), micro-stamping techniques (see, e.g., Kumar et al. (1994) *Langmuir* 10(5):1498–1511; Kumar et al. (1993)*Appl. Phys. Lett.* 63(14):2002–2004), and the like.

V. Reading the Sensor

The sensors of this invention are read using standard methods well known to those of skill in the art. In particular, the sensors of this invention provide a signal that is a change in conductivity (resistivity) of the sensor element(s) as target analytes are bound.

In preferred embodiments, the sensors of this invention are read using techniques including, but not limited to amperommetry, voltammetry, capacitance, and impedence. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential; pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic: chronopotentiometry and amperometry, AC polography, chronogalvametry, and chronocoulometry); AC impedance measurement; capacitance measurement; and photoelectrochemistry.

In a preferred embodiment, monitoring electron transfer through the binding agent/target analyte complex is via amperometric detection. In certain embodiments, a preferred amperometric detector resembles the numerous enzyme-based biosensors currently used to monitor blood glucose, for example. This method of detection involves applying a potential (as compared to a separate reference electrode) between the two electrodes comprising a sensor element of this invention. Electron transfer of differing efficiencies is induced in samples in the presence or absence of target nucleic add; that is, where the binding agent is a nucleic acid, the single stranded binding agent exhibits a different rate than the probe hybridized to the target sequence. The differing efficiencies of electron transfer result in differing currents being generated in the electrode.

In preferred embodiments, devices for measuring electron transfer amperometrically involves sensitive (nanoamp to picoamp) current detection and include al means of controlling the voltage potential, usually a potentiostat.

In other preferred embodiments, alternative electron detection modes are utilized. For example, potentiometric (or voltammetric) measurements involve non-faradaic (no net current flow) processes and are utilized traditionally in pH and other ion detectors. Similar sensors can be used to monitor electron transfer the binding agent/target analyte complex. In addition, other properties of insulators (such as resistance) and of conductors (such as conductivity, impedance and capacitance) can be used to monitor electron transfer through the binding agent/target analyte complex. Finally, any system that generates a current (such as electron transfer) also generates a small magnetic field, which can be monitored in some embodiments.

In preferred embodiments, the relatively fast rates of electron transfer through the binding agent/target analyte complex can facilitate analysis in the frequency (time) domain and thereby dramatically improve signal to noise (S/N) ratios. Thus, in certain embodiments, electron transfer is initiated and detected using alternating current (AC) methods. In general, the use of AC techniques can result in good signals and low background noise. Without being bound by theory, there are a number of possible contributors to background noise, or "parasitic" signals, i.e. detectable signals that are inherent to the system but are not the result of the presence of the target sequence.

However, all of the contributors to parasitic noise generally give relatively fast signals; that is, the rate of electron transfer through the binding agent/target analyte complex is generally significantly slower than the rate of electron transfer of the parasitic components, such as the contribution of charge carriers in solution, and other "short circuiting" mechanisms. As a result, the parasitic components are generally all phase related; that is, they exhibit a constant phase delay or phase shift that will scale directly with frequency. The binding agent/target analyte complex, in contrast, exhibits a time delay between the input and output signals, which is independent of frequency. Thus, signal produced by analyte binding will remain relatively constant and relatively large as compared to parasitic background. As a consequence, at different frequencies, the phase of the system will change. This is very similar to the time domain detection used in fluorescent systems.

This difference can be exploited in various methods to decrease the signal to noise ratio. Accordingly, the preferred detection methods comprise applying an AC input signal to a binding agent/target analyte complex. The presence of the binding agent/target analyte complex is detected via an output signal characteristic of electron transfer through the binding agent/target analyte complex; that is, the output signal is characteristic of the binding agent/target analyte complex rather than the parasitic components or unbound binding agent. Thus, for example, the output signal will exhibit a time delay dependent on the rate of electron transfer through the binding agent/target analyte complex.

In certain preferred embodiments, the input signals are applied at a plurality of frequencies, since this again allows the distinction between true signal and noise. "Plurality" in this context means at least two, and preferably more, frequencies. In general, the AC frequencies will range from about 0.1 Hz to about 10 mHz, with from about 1 Hz to 100 KHz being preferred.

In certain preferred embodiments, data analysis is preformed in the time domain (frequency domain). Thus, for example, cyclic voltammetry is performed where the signal is analyzed at a harmonic of the fundamental frequency. Such measurements can significantly improve the signal to noise (S/N) ratio.

In preferred embodiments, a cyclic (e.g., sinusoidal sweeping voltage) is applied to the electrode. The response of the binding agent/target analyte complex to the sinusoidal voltage is selectively detected at a harmonic of the fundamental frequency of the cyclic voltage rather than at the fundamental frequency. As a result, a complete frequency spectrum can be obtained within one cycle.

The step of selectively detecting the voltammetric response comprises the step of selectively detecting a current flowing through the binding agent/target analyte complex at a harmonic of the fundamental frequency. Preferably the harmonic comprises at least one harmonic of the current above the fundamental frequency. Typically, the signal is monitored at harmonics at and above the second harmonic of the fundamental frequency. In general, the step of selectively detecting the voltammetric response comprises the step of detecting a plurality of higher harmonics of the fundamental frequency within a frequency spectrum of a current flowing through the analyte, either through the use of multiple lock-in detectors, or via data acquisition in the time domain, followed by, e.g., Fourier transformation and convolution via computer based methods. Methods of cyclic voltammetry are known to those of skill in the art and describe in detail in U.S. Pat. Nos. 6,208,553 and 5,958,215

VI. Analyte Detection/quantification

A) Sample Preparation

Virtually any sample can be analyzed using the devices and methods of this invention. Such samples include, but are not limited to body fluids or tissues, water, food, blood, serum, plasma, urine, feces, tissue, saliva, oils, organic solvents, earth, water, air, or food products. In a preferred embodiment, the sample is a biological sample. The term "biological sample", as used herein, refers to a sample obtained from an organism or from components (e.g., cells) of an organism. The sample may be of any biological tissue or fluid. Frequently the sample will be a "clinical sample" which is a sample derived from a patient. Such samples include, but are not limited to, sputum, cerebrospinal fluid, blood, blood fractions (e.g. serum, plasma), blood cells (e.g., white cells), tissue or fine needle biopsy samples, urine, peritoneal fluid, and pleural fluid, or cells therefrom. Biological samples may also include sections of tissues such as frozen sections taken for histological purposes.

Biological samples, (e.g. serum) may be analyzed directly or they may be subject to some preparation prior to use in the assays of this invention. Such preparation can include, but is not limited to, suspension/dilution of the sample in water or an appropriate buffer or removal of cellular debris, e.g. by centrifugation, or selection of particular fractions of the sample before analysis.

B) Sample Delivery into system

The sample can be introduced into the devices of this invention according to standard methods well known to those of skill in the art. Thus, for example, the sample can be introduced into the channel through an injection port such as those used in high pressure liquid chromatography systems. In another embodiment the sample can be applied to a sample well that communicates to the channel. In still another embodiment the sample can be pumped into the channel. Means of introducing samples into channels are well known and standard in the capillary electrophoresis and chromatography arts.

C) Sample Reaction with the Binding Agent

The analyte containing sample is provided to the sensor element in conditions compatible with or that facilitate binding of the analyte to the binding agent comprising the sensor element. Thus, for example, where the sensor element is an antibody or protein, reaction conditions are provided at the sensor element that facilitate antibody binding. Such, reaction conditions are well known to those of skill in the art (see, e.g., Techniques for using and manipulating antibodies are found in Coligan (1991) *Current Protocols in Immunology* Wiley/Greene, N.Y.; Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497, and the like).

Similarly, where the binding agent is a nucleic acid the sensor element is maintained under conditions that facilitate binding of the target nucleic acid (analyte) to the binding agent comprising the sensor element(s). Stringency of the reaction can be increased until the sensor shows adequate/desired specificity and selectivity. Conditions suitable for nucleic acid hybridizations are well known to those of skill in the art (see, e.g., Berger and Kimmel, *Guide to Molecular Cloning Techniques, Methods in Enzymology* 152 Academic Press, Inc., San Diego, Calif.; Sambrook et al. (1989) *Molecular Cloning—A Laboratory Manual* (2nd ed.) Vol. 1–3, Cold Spring Harbor Laboratory, Cold Spring Harbor Press, N.Y.; Ausubel et al. (1994) *Current Protocols in Molecular Biology*, Current Protocols, a joint venture between Greene Publishing Associates, Inc. and John Wiley & Sons, Inc.; U.S. Pat. No. 5,017,478; European Patent No. 0,246,864, and the like).

Once the analyte is bound to the binding agent in the sensor element, the sensor is optionally dehydrated and/or stored and/or read.

Analyte Detection/quantitation

Once introduced into the sensors of this invention, the sample is detected/quantified using standard methods, e.g. as described above, e.g. amperometry, voltammetry, coulometry, etc. The measurement results can be compared to a standard curve, i.e. a series or measurement results plotted as a function of analyte concentration, which permits determination of analyte concentration. The standard curve can be calculated by/stored in the device performing data acquisition.

V. Cassettes

In certain embodiments, this invention provides cassettes comprising one or more sensor elements or sensor element arrays according to this invention. In preferred embodiments, cassettes include one or more biomolecules 14 and/or one or more working electordes 10, 12 and/or biasing electrodes 22.

Thus, for example in certain embodiments, a cassette with comprise a plurality of biomolecules 14, that are each attached to a pair of electrodes. Counter electrodes are optinally provided, e.g. integrated in the layer comprising the working electrodes or provided as a component of a second layer comprising the cassette.

In a preferred embodiment, a cassette or apparatus of the invention comprises a sample port and/or reservoir and one or more channels for sample delivery onto the sensor element(s) present in the cassette. The means for sample delivery can be stationary or movable and can be any known in the art, including but not limited to one or more inlets, holes, pores, channels, pipes, microfluidic guides (e.g., capillaries), tubes, and the like.

The channel(s) comprising the cassette of this invention can comprise a channel network, e.g., one or more channels, preferably microchannels. Typically included within a given channel network are channels or reservoirs in which the desired analysis is to take place (analysis channels), and thus the sensor elements of this invention are disposed. Also, optionally included are channels for delivering reagents, buffers, diluents, sample material and the like to the analysis channels.

The cassettes of this invention optionally include separation channels or matrices separating/fractionating materials transported down the length of these channels, for analysis, i.e., size or charged based fractionation of materials, e.g., nucleic acids, proteins etc. Suitable separation matrices include, e.g., GeneScan.TM. polymers (Perkin Elmer-Applied Biosystems Division, Foster City, Calif.). Alternatively, analysis channels are devoid of any separation matrix, and instead, merely provide a channel within which an interaction, reaction etc., takes place. Examples of microfluidic devices incorporating such analysis channels are described in, e.g., PCT Application No. WO 98/00231, and U.S. Pat. No. 5,976,336.

Fluids can be moved through the cassette channel system by a variety of well known methods, for example: pumps, pipettes, syringes, gravity flow, capillary action, wicking, electrophoresis, electroosmosis, pressure, vacuum, etc. The means for fluid movement may be located on the cassette or on a separate unit.

The sample can be placed on all of the sensor elements. Alternatively, a sample may be placed on particular sensor elements, e.g., by a capillary fluid transport means. Alternatively, samples may be placed on the sensor element (s) by an automatic pipetter for delivery of fluid samples directly to sensor array, or into a reservoir in a cassette or cassette holder for later delivery directly to the sensor element(s).

The cassettes of this invention can be fabricated from a wide variety of materials including, but not limited to glass, plastic, ceramic, polymeric materials, elastomeric materials, metals, carbon or carbon containing materials, alloys, composite foils, silicon and/or layered materials. Supports may have a wide variety of structural, chemical and/or optical properties. They may be rigid or flexible, flat or deformed, transparent, translucent, partially or fully reflective or opaque and may have composite properties, regions with different properties, and may be a composite of more than one material.

Reagents for conducting assays may be stored on the cassette and/or in a separate container. Reagents can be stored in a dry and/or wet state. In one embodiment, dry reagents in the cassette are rehydrated by the addition of a test sample. In a different embodiment, the reagents are stored in solution in "blister packs" which are burst open due to pressure from a movable roller or piston. The cassettes may contain a waste compartment or sponge for the storage of liquid waste after completion of the assay. In one embodiment, the, cassette includes a device for preparation of the biological sample to be tested. Thus, for example, a filter may be included for removing cells from blood. In another example, the cassette may include a device such as a precision capillary for the metering of sample.

A cassette or apparatus of the invention can, optionally, comprise reference electrodes, e.g., Ag/AgCl or a saturated calomel electrode (SCE) and/or various biasing/counter-electrodes.

The cassette can also comprise more one layer of electrodes. Thus, for example, different electrode sets (e.g. arrays of sensor elements) can exist in different lamina of the cassette and thus form a three dimensional array of sensor elements.

Integrated Assay Device/apparatus

State-of-the-art chemical analysis systems for use in chemical production, environmental analysis, medical diagnostics and basic laboratory analysis are preferably capable of complete automation. Such total analysis systems (TAS) (Fillipini et al. (1991) *J. Biotechnol.* 18: 153; Garn et al (1989) *Biotechnol. Bioeng.* 34: 423; Tshulena (1988) *Phys. Scr.* T23: 293; Edmonds (1985) *Trends Anal. Chem.* 4: 220; Stinshoff et al. (1985) *Anal. Chem.* 57:114R; Guibault (1983) *Anal. Chem Symp. Ser.* 17: 637; Widmer (1983) *Trends Anal. Chem.* 2: 8) automatically perform functions ranging from introduction of sample into the system, transport of the sample through the system, sample preparation, separation, purification and detection, including data acquisition and evaluation.

Recently, sample preparation technologies have been successfully reduced to miniaturized formats. Thus, for example, gas chromatography (Widmer et al. (1984) *Int. J. Environ. Anal. Chem.* 18: 1), high pressure liquid chromatography (Muller et al. (1991) *J. High Resolut. Chromatogr.* 14: 174; Manz et al. (1990) *Sensors & Actuators* B1:249; Novotny et al., eds. (1985) *Microcolumn Separations: Columns, Instrumentation and Ancillary Techniques J. Chromatogr. Library*, Vol. 30; Kucera, ed. (1984) *Micro-Column High Performance Liquid Chromatography*, Elsevier, Amsterdam; Scott, ed. (1984) *Small Bore Liquid Chromatography Columns: Their Properties and Uses*, Wiley, N.Y.; Jorgenson et al. (1983) *J. Chromatogr.* 255: 335; Knox et al. (1979) *J. Chromatogr.* 186:405; Tsuda et al. (1978) *Anal Chem.* 50: 632) and capillary electrophoresis (Manz et al. (1992) *J. Chromatogr.* 593: 253; Olefirowicz et al. (1990) *Anal. Chem.* 62: 1872; *Second Int'l Symp. High-Perf. Capillary Electrophoresis* (1990) *J. Chromatogr.* 516; Ghowsi et al. (1990) *Anal. Chem.* 62:2714) have been reduced to miniaturized formats.

Similarly, in certain embodiments, this invention provides an integrated assay device (e.g., a TAS) for detecting and/or quantifying one or more analytes using the sensor elements, sensor element arrays, or cassettes of this invention.

Thus, in certain embodiments, the cassettes of this invention are designed to be inserted into an apparatus, that contains means for reading one or more sensor elements comprising a cassette of this invention. The apparatus, optionally includes means for applying one or more test samples onto the sensor elements or into a receiving port or reservoir and initiating detecting/quantifying one or more analytes. Such apparatus may be derived from conventional apparatus suitably modified according to the invention to conduct a plurality of assays based on a support or cassette. Modifications required include the provision for, optional, sample and/or cassette handling, multiple sample delivery, multiple electrode reading by a suitable detector, and signal acquisition and processing means.

Preferred apparatus, in accordance with this invention, thus typically include instrumentation suitable for performing electrochemical measurements and associated data acquisition and subsequent data analysis.

Preferred apparatus also provide means to hold cassettes, optionally provide reagents and/or buffers and to provide conditions compatible with binding agent/target analyte binding reactions.

A preferred apparatus also comprises an electrode contact means able to electrically connect the array of separately addressable electrode connections of the cassette to an electronic-voltage/waveform generator, e.g., potentiostat. The waveform generator meal s delivers signals sequentially or simultaneously to independently read a plurality of sensor elements in the cassette.

The apparatus optionally comprises a digital computer or microprocessor to control the functions of the various components of the apparatus.

The apparatus also comprises signal processing means. In one embodiment, and simply by way of example, the signal processing means comprises a digital computer for transferring, recording, analyzing and/or displaying the results of each assay.

The sensor element arrays of this invention are particularly well suited for use as detectors in "low sample volume" instrumentation. Such applications include, but are not limited to genomic applications such as monitoring gene expression in plants or animals, parallel gene expression studies, high throughput screening, clinical diagnosis, single nucleotide polymorphism (SNP) screening, genotyping, and the like. Certain particularly preferred embodiments, include miniaturized molecular assay systems, so-called labs-on-a-chip, that are capable of performing thousands of analyses simultaneously Kits In certain embodiments, this invention provides kits for practice of the methods and/or assembly of the devices described herein. Preferred kits comprise a container containing one or more sensor elements according to the present invention. The sensor elements can be components of a sensor array and/or can comprise a sensor cassette as describe herein. In certain embodiments, the kits, optionally, include one or more reagents and/or buffers for use with the sensors of this invention. The kits can optionally include materials for sample acquisition, processing, and the like.

The kits can also include instructional materials containing directions (i.e., protocols) for the practice of the assay methods of this invention the use of the cassettes described herein, methods of assembling sensor elements into various instruments, and the like. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1
Sensor Element Formation

Alternating layers of insulators and conductors are formed by sputtering or vapor deposition (e.g. as described in U.S. Pat. No. 5,414,588. The layers consist of a substrate (Alkali-free borosilicate glass (Shott AF45)), followed by a first conductor, then an insulator, followed by a second conductor and so forth. The first conductor plus insulator, and the second conductor plus a second insulator comprise one iteration. Iterations are repeated until the desired number of lamina is achieved.

Figure 12A:
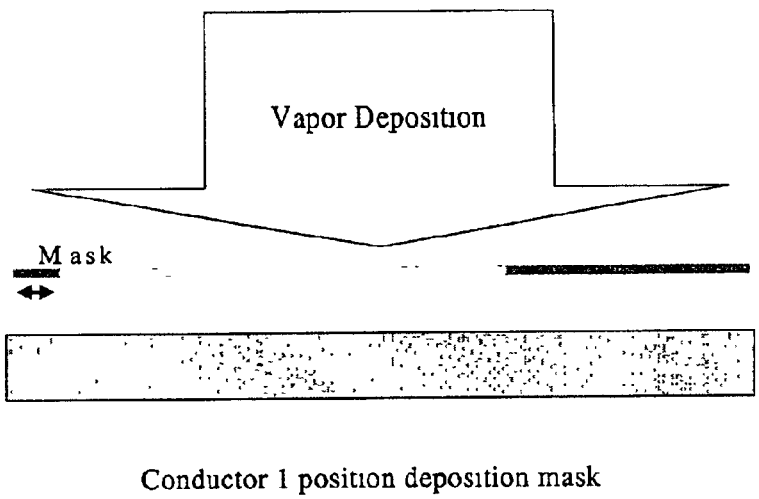
FIGS. 12A, 12B, 12C, and 12D illustrate the deposition of alternating conductor and insulator layers.
Figure 12B:
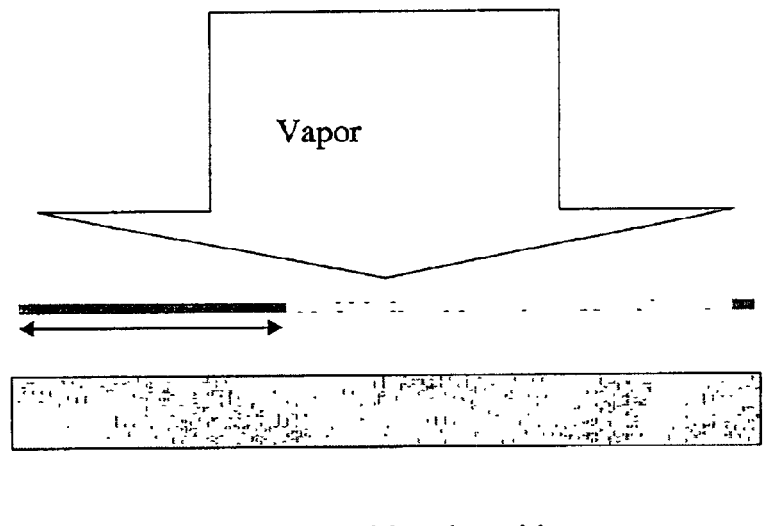
Figure 12C:
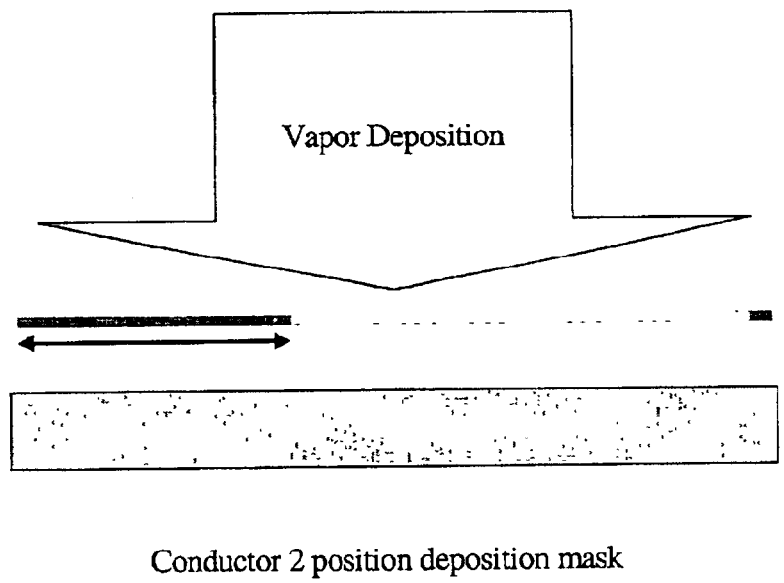

The position of the conductors and insulators is determined by a mask. Thus, as a illustrated in FIG. 12A, conductor 1 has a designated mask and/or mask position of the mask determining the location of its deposition. Similarly, the insulator position is determined by the use of a second mask, as illustrated in FIG. 12B, and the position of conductor 2 is determined by a third mask as illustrated in FIG. 12C. The masks are reused for each subsequent iteration for a total of ten iterations.

Figure 12D:
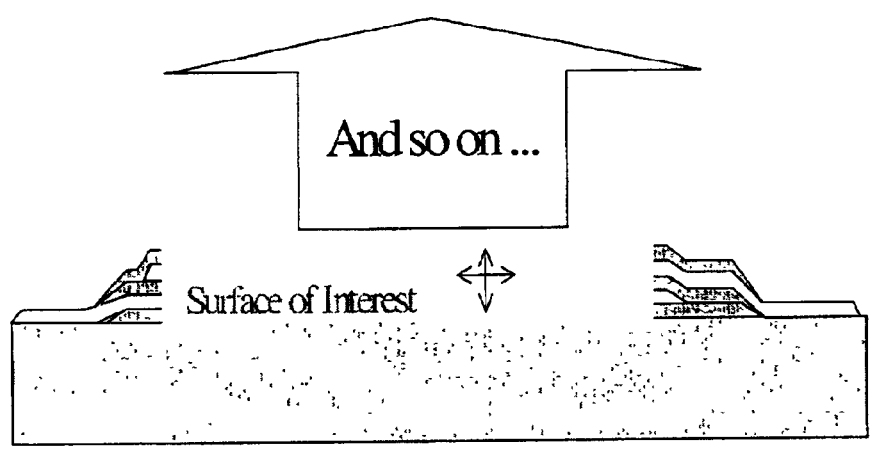

The sputtering process results in a multi-laminar structure of alternating conducting and insulating layers where the first conductor layers are connected to each other and the second layers to be connected to each other, but not to the first conductor layers (see. FIG. 12D) similar to the capacitor described in U.S. Pat. No. 5,414,588.

The conductors are fabricated of gold, and the insulator layers are made of glass or polystyrene or teflon.

The multilayer structure is cut to expose the thin layers of conductors and insulators. The exposed surface is then polished smooth. In selected structures, the insulator layers are etched further to form a channel between the conductive layers.

The first conductor layers are connected to a first macro-electrode using common semi-conductor etching methods. The second conductor layers are connected to a second macro-electrode also using common semi-conductor etching methods.

The macro-electrodes are connected to a voltage source and tested for non-conductance using an EG&G High Speed Potentiostat/Galvanostat (PerkinElmer Model 283).

Analyte Detection

The multilayer electrode face is contacted with a capture probe solution comprising 30 mer oligonucleotides. The 5 prime end of the oligonucleotides is derivatized with an electrolabile an alkyl- or aryl chloroformate, which can be removed at −1.5 volts in the presence of $LiClO_4/CH_3OH$ to reveal a thiol group which can then form a covalent bond with a gold electrode.

The 3 prime end of the oligonucleotide is derivatized with another electrolabile group such as S-benzyloxycarbonyl moiety which can removed at −2.6 volts in DMF and tetrabutyl ammonium chloride. Each of the electrolabile groups is cleaveable at a unique voltage.

The first conductor is biased with the activation voltage of the 5 prime electrolabile group on the capture probe thereby exposing the thiol group which then attaches to the first conductor.

The second conductor is biases with the activation voltage of the 3 prime electrolabile group of the capture probe thereby attaching the probe to connect to the second conductor. The electrodes are then dried under nitrogen or argon.

The electrodes are connected to a macro electrodes to a voltage source and tested for non-conductance, or a background conductance, is measured using a high-speed potentiostat/galvanostat (e.g. Perkin-Elmer, Model 283).

The solution comprising the analyte (a nucleic acid comprising a sequence complementary to the capture probe) is contacted with the capture probe and allowed to hybridize to the capture probe on the electrodes.

The electrodes are dried again under nitrogen or argon. A voltage (4–7 volts) is applied again to the electrodes and the current is measured. The measured current of the hybridized nucleic acids is significantly greater than the current measured for the unhybridized electrodes.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A molecular sensing apparatus comprising:
   a plurality of electrode pairs, wherein the electrode pairs comprise:
   a first electrode;
   a second electrode; and
   an insulator between said first electrode and said second electrode, wherein said insulator comprises a channel between said first electrode and said second electrode and wherein said first electrode and said second electrode are separated by less than 30 nanometers and said apparatus is configured by having parallel electrode portions to permit the formation of a plurality of independent, electrically coupled binding agent/analyte complexes electrically in parallel between said first electrode and said second electrode.

2. The molecular sensing apparatus of claim 1, wherein said insulator has a resistivity greater than $10^{-3}$ ohm-meters.

3. The molecular sensing apparatus of claim 1, wherein said insulator is selected from the group consisting of $SiO_2$, $TiO_2$, $ZrO_2$, quartz, porcelain, ceramic, polystyrene, TEFLON, and an insulating oxide or sulfide of a transition metal in the periodic table of the elements.

4. The molecular sensing apparatus of claim 1, wherein said first electrode and said second electrode are separated by a distance in the range of 1 Angstrom to $10^{10}$ Angstroms.

5. The molecular sensing apparatus of claim 1, wherein at least one of said first electrode and said second electrode has a resistivity of less than $10^{-2}$ ohm-meters.

6. The molecular sensing apparatus of claim 1, wherein at least one of said first electrode and said second electrode has a resistivity of less than $10^{-3}$ ohm-meters.

7. The molecular sensing apparatus of claim 1, wherein said first electrode and said second electrode each comprises a material selected from the group consisting of ruthenium, osmium, cobalt, rhodium, rubidium, lithium, sodium, potassium, vanadium, cesium, beryllium, magnesium, calcium, chromium, molybdenum, silicon, germanium, aluminum, iridium, nickel, palladium, platinum, iron, copper, titanium, tungsten, silver, gold, zinc, cadmium, indium tin oxide, carbon, and carbon nanotube.

8. The molecular sensing apparatus of claim 1, wherein at least one of said first electrode and said second electrode is functionalized with a chemical group that can be derivatized or crosslinked.

9. The molecular sensing apparatus of claim 8, wherein said chemical group is selected from the group consisting of a sulfate, a sulfhydryl, an amine, an aldehyde, a carboxylic acid, a phosphate, a phosphonate, an alkene, an alkyne, a hydroxyl, a bromine, an iodine, a chlorine, a light-activatable group, and a group activatable by an electric potential.

10. The molecular sensing apparatus of claim 1, wherein at least one of said first electrode and said second electrode bears a self-assembled monolayer (SAM).

11. The molecular sensing apparatus of claim 10, wherein said SAM comprises a compound selected from the group consisting of an alkanethiol, a phospholipid, a bola amphiphile, and an oligo (phenylenevinylene).

12. The molecular sensing apparatus of claim 1, further comprising a substrate that supports the first electrode and the second electrode, wherein the first electrode and the second electrode are integrated with the substrate.

13. The molecular sensing apparatus of claim 1, wherein the first electrode and the second electrode are integrated with the insulator to form a substrate.

14. The molecular sensing apparatus of claim 1, wherein said first electrode comprises a surface with a shape selected from the group consisting of convex, concave, textured, corrugated, patterned uniformly, and randomly patterned.

15. The molecular sensing apparatus of claim 1, wherein said first electrode and said second electrode are oriented in a formation selected from the group consisting of annular, planar, and orthogonal.

16. The molecular sensing apparatus of claim 1, wherein the first electrode has a first surface and a said second electrode has a second surface, wherein the first surface is not coplanar to the second surface.

17. The apparatus of claim 1, wherein said at least one electrode pair comprises a first electrode pair and a second electrode pair.

18. The molecular sensing apparatus of claim 1, wherein said one or more electrode pairs are at least 10 electrode pairs.

19. The molecular sensing apparatus of claim 1, wherein said one or more electrode pairs are at least 1,000 electrode pairs.

20. The molecular sensing apparatus of claim 1, wherein said one or more electrode pairs comprises about $10^2$ to $10^{10}$ electrode pairs.

21. The molecular sensing apparatus of claim 1, the molecular sensing apparatus further comprising a measurement device electrically coupled to each first electrode and to each second electrode of each electrode pair in said at least one electrode pair.

22. The molecular sensing apparatus of claim 21, wherein said measurement device measures an electromagnetic property selected from the group consisting of direct electric current, alternating electric current, permitivity, resistivity, electron transfer, electron tunneling, electron hopping, electron transport, electron conductance, voltage, electrical impedance, signal loss, dissipation factor, resistance, capacitance, inductance, magnetic field, electrical potential, charge and magnetic potential.

23. The molecular sensing apparatus of claim 1, further comprising an electrical circuit electrically coupled to the first electrode and the second electrode.

24. The molecular sensing apparatus of claim 23, wherein said electrical circuit comprises an electric signal gating system.

25. The molecular sensing apparatus of claim 24, wherein said electric signal gating system comprises a CMOS gating system.

26. The apparatus of claim 17, wherein
a first biological macromolecule is attached to the first electrode and the second electrode in the first electrode pair, and
a second biological macromolecule is attached to the first electrode and the second electrode in the second electrode pair; wherein the first biological molecule and the second biological molecule are the same.

27. The apparatus of claim 17, wherein
a first biological macromolecule is attached to the first electrode and the second electrode in the first electrode pair, and
a second biological macromolecule is attached to the first electrode and the second electrode in the second electrode pair; wherein the first biological molecule and the second biological molecule are different.

28. The molecular sensing apparatus of claim 1, further comprising a computer electrically coupled to the first electrode and the second electrode.

29. The molecular sensing apparatus of claim 1, wherein at least one of the first electrode and the second electrode comprises a semiconductor material.

30. The molecular sensing apparatus of claim 29, wherein said semiconductor material has a resistivity ranging from $10^{-6}$ω-m to $10^7$Ω-m.

31. The molecular sensing apparatus of claim 29, wherein the semiconductor material is selected from the group consisting of silicon, dense silicon carbide, boron carbide, $Fe_3O_4$, germanium, silicon germanium, silicon carbide, tungsten carbide, titanium carbide, indium phosphide, gallium nitride, gallium phosphide, aluminum phosphide, aluminum arsenide, mercury cadmium telluride, tellurium, selenium, ZnS, ZnO, ZnSc. CdS, ZnTc, GaSc, CdSe, CdTe, GaAs, InP, GaSb, EnAs, Te, PbS, InSb, PbTe, PbSe, and tungsten disulfide.

32. A molecular sensing apparatus comprising a plurality of electrode pairs in an insulating substrate,
  wherein a first electrode pair in said plurality of electrode pairs comprises a first electrode and a second electrode,
  wherein said first electrode and said second electrode are separated by less than 30 nanometers and said apparatus is configured by having parallel electrode portions to permit the formation of a plurality of independent, electrically coupled binding agent/analyte complexes electrically in parallel between said first electrode and said second electrode.

33. The molecular sensing apparatus of claim 32 wherein a biological macromolecule connects said first electrode and said second electrode.

34. The molecular sensing apparatus of claim 33 wherein said biological macromolecule is a nucleic acid.

35. The molecular sensing apparatus of claim 34 wherein said nucleic acid is a deoxyribonucleic acid or a ribonucleic acid.

36. The molecular sensing apparatus of claim 32 wherein at least one of said first electrode and said second electrode has a resistivity of less than $10^{-3}$ ohm-meters.

37. The molecular sensing apparatus of claim 32 wherein said first electrode and said second electrode comprise a material selected from the group consisting of ruthenium, osmium, cobalt, rhodium, rubidium, lithium, sodium, potassium, vanadium, cesium, beryllium, magnesium, calcium, chromium, molybdenum, silicon, germanium, aluminum, iridium, nickel, palladium, platinum, iron, copper, titanium, tungsten, silver, gold, zinc, cadmium, indium tin oxide, carbon, and carbon nanotube.

38. The molecular sensing apparatus of claim 32 wherein at least one of said first electrode and said second electrode is functionalized with a chemical group that can be derivatized or crosslinked.

39. The molecular sensing apparatus of claim 38 wherein said chemical group is a sulfate, a sulfhydryl, an amine, an aldehyde, a carboxylic acid, a phosphate, a phosphonate, an alkene, an alkyne, a hydroxyl, a bromine, an iodine, a chlorine, a light-activatable group, or a group activatable by an electric potential.

40. The molecular sensing apparatus of claim 32 wherein at least one of said first electrode and said second electrode is coated with a self-assembled monolayer.

41. The molecular sensing apparatus of claim 40 wherein said self-assembled monolayer comprises a compound selected from the group consisting of an alkanethiol, a phospholipid, a bola amphiphile, and an oligo (phenylenevinylene).

42. The molecular sensing apparatus of claim 33 wherein the biological macromolecule is attached to the first electrode by a thiol group.

43. The molecular sensing apparatus of claim 34 wherein the biological macromolecule is attached to the first electrode by a phosphonate.

44. The molecular sensing apparatus of claim 34 wherein the biological macromolecule is attached to said first electrode by a linker.

45. The molecular sensing apparatus of claim 44 wherein said linker is selected from the group consisting of DFDNB, DST, ABH, ANB-NOS, EDC, NHS-ASA, and SIA.

46. The molecular sensing apparatus of claim 32 wherein the first electrode has a first surface and the second electrode has a second surface, and wherein the first surface is not coplanar to the second surface.

47. The molecular sensing apparatus of claim 32 wherein said one or more electrode pairs comprise at least three electrode pairs.

48. The molecular sensing apparatus of claim 32 wherein said one or more electrode pairs comprise at least 10,000 electrode pairs.

49. The molecular sensing apparatus of claim 32 wherein said one or more electrode pairs comprises $10^2$ to $10^{10}$ electrode pairs.

50. The molecular sensing apparatus of claim 32 the apparatus further comprising a measurement device electrically coupled to the first electrode and to the second electrode said first electrode pair.

51. The molecular sensing apparatus of claim 50 wherein said measurement device measures an electromagnetic property selected from the group consisting of direct electric current, alternating electric current, permitivity, resistivity, electron transfer, electron tunneling, electron hopping, electron transport, electron conductance, voltage, electrical impedance, signal loss, dissipation factor, resistance, capacitance, inductance, magnetic field, electrical potential, charge and magnetic potential.

52. The molecular sensing apparatus of claim 32 further comprising an electrical circuit electrically coupled to the first electrode and the second electrode of said first electrode pair.

53. The molecular sensing apparatus of claim 52 wherein said electrical circuit comprises an electric signal gating system.

54. The molecular sensing apparatus of claim 32 wherein said biological molecule connects to said first electrode and said second electrode in said first electrode pair.

55. The molecular sensing apparatus of claim 32 wherein
  a first biological macromolecule is attached to said first electrode in said first electrode pair, and
  a second biological macromolecule is attached to said second electrode in said first electrode pair.

56. The molecular sensing apparatus of claim 32 further comprising a computer electrically coupled to the first electrode and the second electrode of at least one electrode pair in said one or more electrode pairs.

57. The molecular sensing apparatus of claim 32 wherein at least one of the first electrode and the second electrode in an electrode pair in said one or more electrode pairs comprises a semiconductor material.

58. The molecular sensing apparatus of claim 57 wherein said semiconductor material has a resistivity between $10^{-6}$Ω-m and $10^{-7}$Ω-m.

59. The molecular sensing apparatus of claim 57 wherein the semiconductor material is selected from the group, consisting of silicon, dense silicon carbide, boron carbide, $Fe_3O_4$, germanium, silicon germanium, silicon carbide, tungsten carbide, titanium carbide, indium phosphide, gallium nitride, gallium phosphide, aluminum phosphide, aluminum arsenide, mercury cadmium telluride, tellurium, selenium, ZnS, ZnO, ZnSe, CdS, ZnTe, GaSe, CdSe, CdTe, GaAs, InP, GaSb, EnAs, Te, PbS, InSb, PbTe, PbSe, and tungsten disulfide.

60. The molecular sensing apparatus of claim 1, wherein a biological macromolecule or macromolecule/analyte complex connects said first electrode and said second electrode in said first electrode pair.

61. The molecular sensing apparatus of claim 60 wherein said biological macromolecule is selected from the group consisting of a nucleic acid, a protein, a polysaccharide, a lectin, and a sugar.

62. The molecular sending apparatus of claim 60 wherein said biological macromolecule is a deoxyribonucleic acid or a nucleic acid.

63. The molecular sensing apparatus of claim 60 wherein said biological macromolecule is functionalized with a chemical group selected from the group consisting of a sulfate, a sulfhydryl, an amine, an aldehyde, a carboxylic acid, a phosphate, a phosphonate, an alkene, an alkyne, a hydroxyl, a bromine, an iodine, a chlorine, a light-activatable group, and a group activatable by an electric potential.

64. The molecular sensing apparatus of claim 60 wherein the biological macromolecule is attached to the first electrode by a thiol group.

65. The molecular sensing apparatus of claim 60 wherein the biological macromolecule is attached to the first electrode by a phosphorothioate or a phosphonate.

66. The molecular sensing apparatus of claim 60 wherein the biological macromolecule is attached to said first electrode by a linker.

67. The molecular sensing apparatus of claim 66 wherein said linker is selected from the group consisting of DFDNB, DST, ABH, ANB-NOS, EDC, NHS-ASA, and SIA.

68. The molecular sensing apparatus of claim 1 wherein a first biological macromolecule is attached to said first electrode and a second biological macromolecule is attached to said second electrode.

69. The molecular sensing apparatus of claim 1 wherein said first electrode comprises a surface with a shape selected from the group consisting of convex, concave, textured, corrugated, patterned uniformly, and randomly patterned.

70. The molecular sensing apparatus of claim 62 wherein said nucleic acid is deoxyribonucleic acid or ribonucleic acid.

71. The molecular sensing apparatus of claim 1, wherein said first electrode and said second electrode are separated by less than 20 nanometers.

72. The molecular sensing apparatus of claim 71, wherein said first electrode and said second electrode are separated by less than 15 nanometers.

73. The molecular sensing apparatus of claim 72, wherein said first electrode and said second electrode are separated by less than 10 nanometers.

74. The molecular sensing apparatus of claim 32, wherein said first electrode and said second electrode are separated by less than 20 nanometers.

75. The molecular sensing apparatus of claim 74, wherein said first electrode and said second electrode are separated by less than 15 nanometers.

76. The molecular sensing apparatus of claim 75, wherein said first electrode and said second electrode are separated by less than 10 nanometers.

* * * * *

UNITED STATES PATENT AND TRADEMARK OFFICE
CERTIFICATE OF CORRECTION

PATENT NO.    : 6,824,974 B2
DATED         : November 30, 2004
INVENTOR(S)   : Sobha M. Pisharody, Sandeep Kunwar and George T. Mathai It is certified that error appears in the above-identified patent and that said Letters Patent is hereby corrected as shown below:

<u>Column 33,</u>
Line 65, delete "a" before "said"

<u>Column 35,</u>
Lines 55 and 58, please replace "34" with -- 33--

<u>Column 36,</u>
Line 65, please replace "sending" with -- sensing --

Signed and Sealed this

Fifth Day of April, 2005

JON W. DUDAS
*Director of the United States Patent and Trademark Office*